United States Patent
Bouyssou et al.

(10) Patent No.: US 7,160,882 B2
(45) Date of Patent: Jan. 9, 2007

(54) LONG ACTING β-2-AGONISTS AND THEIR USE AS MEDICAMENTS

(75) Inventors: Thierry Bouyssou, Mietingen (DE); Ingo Konetzki, Warthausen (DE); Philipp Lustenberger, Warthausen (DE); Juergen Mack, Biberach-Mettenberg (DE); Andreas Schnapp, Biberach (DE); Dieter Wiedenmayer, Biberach (DE); Christoph Hoenke, Ingelheim (DE); Klaus Rudolf, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/029,451

(22) Filed: Jan. 5, 2005

(65) Prior Publication Data

US 2005/0227975 A1 Oct. 13, 2005

Related U.S. Application Data

(60) Provisional application No. 60/557,081, filed on Mar. 26, 2004.

(30) Foreign Application Priority Data

Jan. 23, 2004 (DE) .................. 10 2004 003 428

(51) Int. Cl.
C07D 413/12 (2006.01)
C07D 413/14 (2006.01)
A61K 31/538 (2006.01)
A61K 31/536 (2006.01)

(52) U.S. Cl. ............ 514/230.5; 544/92; 544/284; 546/158; 514/266.2; 514/266.23; 514/266.3; 514/312

(58) Field of Classification Search ........ 544/92, 544/284; 546/158; 514/230.5, 266.2, 266.23, 514/266.3, 312
See application file for complete search history.

(56) References Cited

U.S. PATENT DOCUMENTS 4,215,119 A * 7/1980 Mentrup et al. ....... 514/230.5

| 4,341,778 | A | 7/1982 | Mentrup et al. |
| 2002/0022625 | A1 | 2/2002 | Schromm et al. |
| 2004/0122108 | A1 | 6/2004 | Bouyssou et al. |
| 2004/0147513 | A1 | 7/2004 | Bouyssou et al. |

FOREIGN PATENT DOCUMENTS

| EP | 0 043 940 | 6/1981 |
| WO | WO 01/83462 | 11/2001 |

OTHER PUBLICATIONS

U.S. Appl. No. 09/836,462, filed Apr. 18, 2001, K. Bozung et al.
U.S. Appl. No. 10/697,525, filed Oct. 30, 2003, T. Bouyssou et al.
U.S. Appl. No. 11/028,264, filed Jan. 3, 2005, T. Bouyssou et al.
U.S. Appl. No. 11/057893, filed Feb. 14, 2005, T. Bouyssou et al.
U.S. Appl. No. 11/074,263, filed Mar. 7, 2005, T. Bouyssou et al.
Kriton Iakovou, et al. "Synthesis of oxypropanolamine derivatives of 3,4-dihydro-2H-1,4-benzoxazine, beta-adrenergic affinity, inotropic, chronotropic and coronary vasodilating activities" Eur. J. Med. Chem. 34, 1999, pp. 903-917.

* cited by examiner

*Primary Examiner*—Kahsay Habte
(74) *Attorney, Agent, or Firm*—Michael P. Morris; Timothy X. Witkowski; Wendy Petka

(57) ABSTRACT

The present invention relates to compounds of formula 1

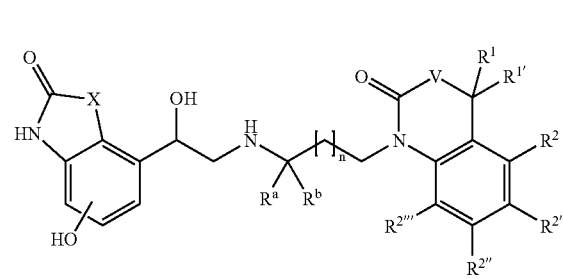

wherein the groups X, $R^a$, $R^b$, $R^1$, $R^{1'}$, $R^2$, $R^{2'}$, $R^{2''}$, $R^{2'''}$, V and n may have the meanings given in the claims and in the specification, and the use thereof as pharmaceutical compositions, particularly for the treatment of inflammatory and obstructive respiratory complaints.

10 Claims, No Drawings

LONG ACTING β-2-AGONISTS AND THEIR USE AS MEDICAMENTS

RELATED APPLICATIONS

Benefit of U.S. Provisional Application Ser No. 60/557,081, filed on Mar. 26, 2004, is hereby claimed, and which application is incorporated herein in its entirety.

FIELD OF THE INVENTION

The present invention relates to compounds of formula 1

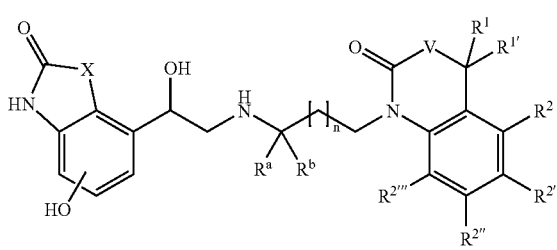

wherein the groups X, $R^a$, $R^b$, $R^1$, $R^{1'}$, $R^2$, $R^{2'}$, $R^{2''}$, $R^{2'''}$, V and n may have the meanings given in the claims and in the specification, processes for preparing them and their use as pharmaceutical compositions, particularly for the treatment of inflammatory and obstructive respiratory complaints.

BACKGROUND OF THE INVENTION

Betamimetics (β-adrenergic substances) are known from the prior art. In this respect reference is made for example to the disclosure of EP 43 940 or WO 01/83462, which propose betamimetics for the treatment of a wide range of diseases.

For the drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the wellbeing of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which are characterised by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day. A further objective of the invention is to prepare new betamimetics which, by virtue of their long-lasting effect, can be used to prepare a drug for administration once a day for the treatment of inflammatory or obstructive respiratory complaints.

In addition to the above objectives, the present invention also sets out to provide betamimetics which are not only exceptionally potent but are also characterised by a high degree of selectivity with respect to the $β_2$-adreno-receptor.

DETAILED DESCRIPTION OF THE INVENTION

Surprisingly it has been found that the above-mentioned objectives are achieved by compounds of general formula 1.

Accordingly, the present invention relates to compounds of general formula 1

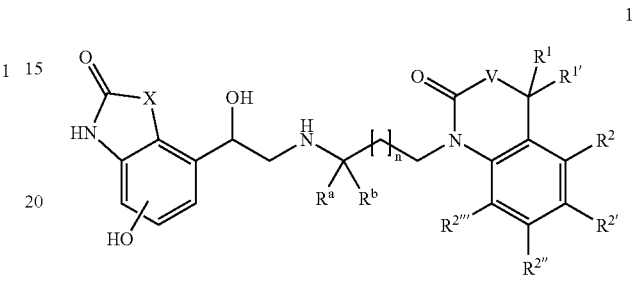

wherein

X denotes a group —O—, —NH—, —$CH_2$—O—, —CHMe-O—, —$C(Me)_2$-O—, —$CH_2$—NH—, —CHMe-NH—, —$C(Me)_2$-NH—, —CH=CH— or —$CH_2$—$CH_2$—;

V denotes a double-bonded group selected from among $CH_2$, NH and O, preferably $CH_2$ and O, particularly preferably O;

$R^a$ and $R^b$ which may be identical or different, denote a group selected from among hydrogen, $C_{1-4}$-alkyl, and halogen-$C_{1-4}$-alkyl, or $R^a$ and $R^b$ together denote a $C_{2-5}$-alkylene-bridge, wherein one or more hydrogen atoms may optionally be replaced by halogen;

$R^1$ and $R^{1'}$ which may be identical or different, denote a group selected from among hydrogen, $C_{1-6}$-alkyl, $C_{3-6}$-cycloalkyl, halogen-$C_{1-6}$-alkyl, halogen-$C_{3-6}$-cycloalkyl or $C_{1-6}$-alkylene-$C_{3-6}$-cycloalkyl, or $R^1$ and $R^{1'}$ together denote a $C_{2-5}$-alkylene-bridge wherein one or more hydrogen atoms may optionally be replaced by halogen;

$R^2$, $R^{2'}$, $R^{2''}$ and $R^{2'''}$ which may be identical or different, denote a group selected from among hydrogen, $C_{1-6}$-alkyl, halogen-$C_{1-6}$-alkylene, OH, HO—$C_{1-6}$-alkylene, —O—$C_{1-6}$-alkyl, $C_{6-10}$-aryl, $C_{6-10}$-aryl-$C_{1-4}$-alkylene, $C_{6-10}$-aryl-$C_{1-6}$-alkylene-O, COOH, COO$C_{1-6}$-alkyl, O—$C_{1-6}$-alkylene-COOH, O—$C_{1-6}$-alkylene-COO$C_{1-6}$-alkyl, NH$SO_2$—$C_{1-6}$-alkyl, CN, $NH_2$, NH—$C_{1-6}$-alkyl, N($C_{1-6}$-alkyl)$_2$, $NO_2$, S—$C_{1-6}$-alkyl, $SO_2$—$C_{1-6}$-alkyl, SO—$C_{1-6}$-alkyl, O(CO)$C_{1-6}$-alkyl, CO$C_{1-6}$-alkyl, NHCO$C_{1-6}$-alkyl or halogen;

n denotes 0, 1 or 2; preferably 1;

optionally in the form of the individual optical isomers, mixtures of the individual enantiomers or racemates, in the form of the free bases or the corresponding acid addition salts with pharmacologically acceptable acids.

Preferred are the compounds of formula 1 wherein

X denotes —O—, —$CH_2$—O—, —$C(Me)_2$-O— or —CH=CH—;

V denotes a double-bonded group selected from the group consisting of $CH_2$, NH and O, preferably $CH_2$ and O, particularly preferably O;

$R^a$ and $R^b$ which may be identical or different, denote a group selected from among hydrogen, $C_{1-4}$-alkyl and fluoro-$C_{1-4}$-alkyl, or $R^a$ and $R^b$ together denote a group selected from —CH$_2$—CH$_2$, —CH$_2$—CH$_2$—CH$_2$—CH$_2$— and —CH$_2$—CH$_2$—CH$_2$—CH$_2$—CH$_2$, wherein one or more hydrogen atoms may optionally be replaced by fluorine or chlorine, preferably fluorine;

$R^1$ and $R^{1'}$ which may be identical or different, denote a group selected from among hydrogen, $C_{1-6}$-alkyl, $C_{3-6}$-cycloalkyl, halogen-$C_{1-6}$-alkyl or $C_{1-6}$-alkylene-$C_{3-6}$-cycloalkyl, or $R^1$ and $R^{1'}$ together denote a group selected from —CH$_2$—CH$_2$, —CH$_2$—CH$_2$—CH$_2$—CH$_2$— and —CH$_2$—CH$_2$—CH$_2$—CH$_2$—CH$_2$, wherein one or more hydrogen atoms may optionally be replaced by fluorine or chlorine, preferably fluorine;

$R^2$, $R^{2'}$, $R^{2''}$ and $R^{2'''}$ which may be identical or different, denote a group selected from among hydrogen, $C_{1-4}$-alkyl, $CF_3$, $CHF_2$, $CH_2F$, OH, —O—$C_{1-4}$-alkyl, phenyl, phenylethyl, benzyl, phenyloxy, benzyloxy, COOH, COO$C_{1-4}$-alkyl, COCH$_2$COOH, OCH$_2$COO$C_{1-4}$-alkyl, NHSO$_2$—$C_{1-4}$-alkyl, fluorine, chlorine or bromine;

n denotes 0, 1 or 2; preferably 1;

optionally in the form of the individual optical isomers, mixtures of the individual enantiomers or racemates, in the form of the free bases or the corresponding acid addition salts with pharmacologically acceptable acids.

Particularly preferred are the compounds of formula 1 wherein

X denotes —O—, —CH$_2$—O—, —C(Me)$_2$-O— or —CH═CH—;

V denotes a double-bonded group selected from among CH$_2$ and O, preferably O;

$R^a$ and $R^b$ which may be identical or different, denote a group selected from among hydrogen, methyl, ethyl and $CF_3$, preferably hydrogen, methyl or ethyl, or $R^a$ and $R^b$ together denote a group selected from —CH$_2$—CH$_2$— and —CH$_2$—CH$_2$—CH$_2$—CH$_2$, preferably —CH$_2$—CH$_2$—;

$R^1$ and $R^{1'}$ which may be identical or different, denote a group selected from among hydrogen, methyl, ethyl, propyl, cyclopropyl or methylcyclopropyl, or $R^1$ and $R^{1'}$ together denote —CH$_2$—CH$_2$—CH$_2$—CH$_2$— or —CH$_2$—CH$_2$—CH$_2$—CH$_2$—CH$_2$—;

$R^2$, $R^{2'}$, $R^{2''}$ and $R^{2'''}$ which may be identical or different, denote a group selected from among hydrogen, methyl, ethyl, propyl, $CF_3$, $CHF_2$, $CH_2F$, OH, methyloxy, ethyloxy, propyloxy, COOH, COOCH$_3$, COOCH$_2$CH$_3$, OCH$_2$COOH, OCH$_2$COOCH$_3$, NHSO$_2$—CH$_3$, fluorine, chlorine or bromine;

n denotes 0, 1 or 2; preferably 1, optionally in the form of the individual optical isomers, mixtures of the individual enantiomers or racemates, in the form of the free bases or the corresponding acid addition salts with pharmacologically acceptable acids.

Of particular importance according to the invention are the compounds of formula 1 wherein $R^a$ and $R^b$ both represent methyl and wherein the groups X, $R^1$, $R^{1'}$, $R^2$, $R^{2'}$, $R^{2''}$, $R^{2'''}$, V and n may have the above-mentioned meanings.

These preferred compounds may be represented by the following general formula 1.1

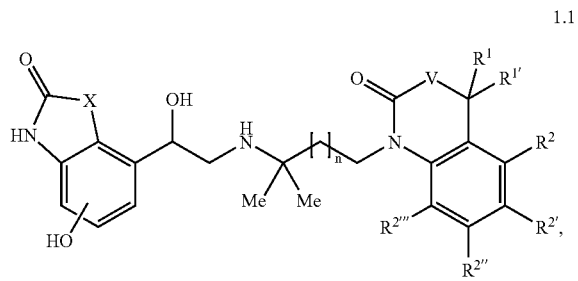

1.1 wherein the groups X, $R^1$, $R^{1'}$, $R^2$, $R^{2'}$, $R^{2''}$, $R^{2'''}$, V and n may have the above-mentioned meanings.

Of particular importance according to the invention are the compounds of formula 1 wherein X corresponds to the group —CH$_2$—O—. These compounds may be represented by the formula 1'

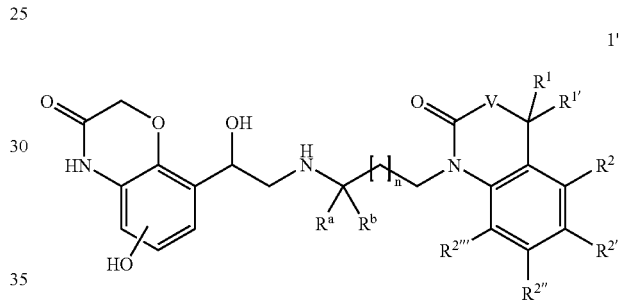

1' wherein the groups $R^a$, $R^b$, $R^1$, $R^{1'}$, $R^2$, $R^{2'}$, $R^{2''}$, $R^{2'''}$ and V are as hereinbefore defined.

Preferred compounds are those of formula 1', wherein $R^a$ and $R^b$ may have the above-mentioned meanings and wherein V denotes a double-bonded group selected from the group consisting of CH$_2$ and O, preferably O;

$R^1$ and $R^{1'}$ which may be identical or different, denote a group selected from among hydrogen, methyl, ethyl, propyl or cyclopropyl, or $R^1$ and $R^{1'}$ together denote —CH$_2$—CH$_2$—CH$_2$—CH$_2$— or —CH$_2$—CH$_2$—CH$_2$—CH$_2$—CH$_2$—;

$R^2$ and $R^{2'''}$ denote hydrogen;

$R^{2'}$ and $R^{2''}$ which may be identical or different, denote a group selected from among hydrogen, methyl, $CF_3$, OH, methyloxy, benzyloxy, COOH, COOCH$_3$ or fluorine;

n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Preferred compounds of formula 1' according to the invention are those wherein $R^a$ and $R^b$ may have the above-mentioned meanings and wherein V denotes a double-bonded group selected from among CH$_2$ and O, preferably O;

$R^1$ and $R^{1'}$ which may be identical or different denote hydrogen, methyl, ethyl, propyl or cyclopropyl, or $R^1$ and $R^{1'}$ together denote —$CH_2$—$CH_2$—$CH_2$—$CH_2$—$CH_2$—;

$R^2$ and $R^{2'}$ denote hydrogen;

$R^{2'}$ and $R^{2'''}$ which may be identical or different, denote a group selected from among hydrogen, methyl, $CF_3$, OH, methyloxy, benzyloxy or fluorine;

n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Of equal importance according to the invention are the compounds of formula 1', wherein $R^a$ and $R^b$ may have the above-mentioned meanings and wherein V denotes the double-bonded group O;

$R^1$ and $R^{1'}$ which may be identical or different, preferably identical, denote hydrogen, methyl, ethyl or propyl;

$R^2$, $R^{2'}$ and $R^{2'''}$ denote hydrogen;

$R^{2'}$ denotes hydrogen, OH, methyloxy or benzyloxy, n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of exceptional importance according to the invention are the compounds of formula 1' wherein $R^a$ and $R^b$ may have the above-mentioned meanings and wherein V denotes the double-bonded group O;

$R^1$ and $R^{1'}$ in each case simultaneously denote hydrogen, methyl, ethyl or propyl;

$R^2$, $R^{2'}$ and $R^{2'''}$ denote hydrogen;

$R^{2'}$ denotes hydrogen, OH or methyloxy, n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of particular importance according to the invention are those compounds of formula 1'wherein $R^a$ and $R^b$ both represent methyl. These compounds may be represented by formula 1.1'

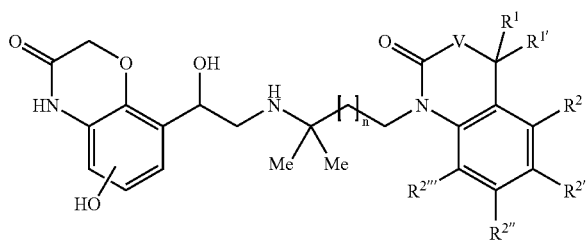

1.1' wherein the groups $R^1$, $R^{1'}$, $R^2$, $R^{2'}$, $R^{2''}$, $R^{2'''}$ and V may have the above-mentioned meanings.

Preferred compounds of formula 1 are those wherein X corresponds to the group —O—. These compounds may be represented by the formula 1"

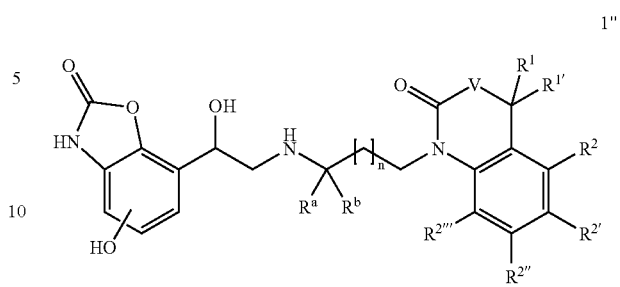

1"

wherein the groups $R^a$, $R^b$, $R^1$, $R^{1'}$, $R^2$, $R^{2'}$, $R^{2''}$, $R^{2'''}$ and V have the above-mentioned meanings.

Particularly preferred are compounds of formula 1", wherein $R^a$ and $R^b$ may have the above-mentioned meanings and wherein V denotes a double-bonded group selected from among $CH_2$ and O, preferably O;

$R^1$ and $R^{1'}$ which may be identical or different denote a group selected from among hydrogen, methyl, ethyl, propyl, cyclopropyl, or $R^1$ and $R^{1'}$ together denote —$CH_2$—$CH_2$—$CH_2$—$CH_2$— or —$CH_2$—$CH_2$—$CH_2$—$CH_2$—$CH_2$—;

$R^2$ and $R^{2'''}$ denote hydrogen;

$R^{2'}$ and $R^{2''}$ which may be identical or different denote a group selected from among hydrogen, methyl, $CF_3$, OH, methyloxy, benzyloxy, COOH, $COOCH_3$ or fluorine;

n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also particularly preferred are compounds of formula 1", wherein $R^a$ and $R^b$ may have the above-mentioned meanings and wherein V denotes a double-bonded group selected from among $CH_2$ and O, preferably O;

$R^1$ and $R^{1'}$ which may be identical or different denote hydrogen methyl, ethyl or propyl, or $R^1$ and $R^{1'}$ together denote —$CH_2$—$CH_2$—$CH_2$—$CH_2$—$CH_2$—;

$R^2$ and $R^{2'''}$ denote hydrogen;

$R^{2'}$ and $R^{2''}$ which may be identical or different denote a group selected from among hydrogen, methyl, $CF_3$, OH, methyloxy, benzyloxy or fluorine;

n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of equal importance according to the invention are the compounds of formula 1", wherein $R^a$ and $R^b$ may have the above-mentioned meanings and wherein V denotes the double-bonded group O;

$R^1$ and $R^{1'}$ which may be identical or different, preferably identical, denote hydrogen, methyl or ethyl;

$R^2$, $R^{2''}$ and $R^{2'''}$ denote hydrogen;

$R^{2'}$ denotes hydrogen, OH, methyloxy or benzyloxy, n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of particular importance according to the invention are those compounds of formula 1″ wherein $R^a$ and $R^b$ both represent methyl. These compounds may be represented by the formula 1.1″

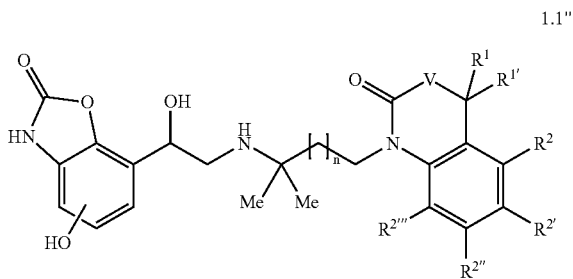

1.1″ wherein the groups $R^1$, $R^{1'}$, $R^2$, $R^{2'}$, $R^{2''}$, $R^{2'''}$ and V may have the above-mentioned meanings.

Also of particular importance according to the invention are compounds of formula 1 wherein X corresponds to the group —CH═CH—. These compounds may be represented by the formula 1‴

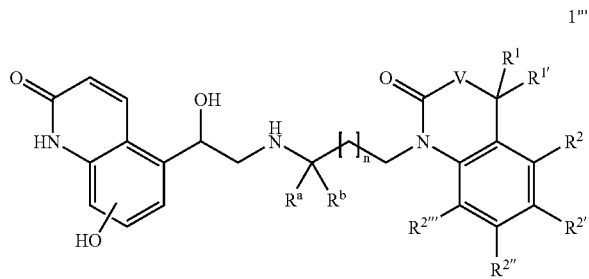

1‴ wherein the groups $R^a$, $R^b$, $R^1$, $R^{1'}$, $R^2$, $R^{2'}$, $R^{2''}$, $R^{2'''}$ and V are as hereinbefore defined.

Preferred are compounds of formula 1‴ wherein $R^a$ and $R^b$ may have the above-mentioned meanings and wherein
V denotes a double-bonded group selected from among $CH_2$ and O, preferably O;
$R^1$ and $R^{1'}$ which may be identical or different denote a group selected from among hydrogen, methyl, ethyl, propyl, cyclopropyl, preferably methyl or ethyl, or
$R^1$ and $R^{1'}$ together denote —$CH_2$—$CH_2$—, —$CH_2$—$CH_2$—$CH_2$—$CH_2$— or —$CH_2$—$CH_2$—$CH_2$—$CH_2$—$CH_2$—;
$R^2$ and $R^{2'''}$ denote hydrogen;
$R^{2'}$ and $R^{2''}$ which may be identical or different denote a group selected from among hydrogen, methyl, $CF_3$, OH, methyloxy, benzyloxy, COOH, $COOCH_3$ or fluorine;
n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Particularly preferred are compounds of formula 1‴, wherein $R^a$ and $R^b$ may have the above-mentioned meanings and wherein
V denotes a double-bonded group selected from the group consisting from $CH_2$ and O, preferably O;

$R^1$ and $R^{1'}$ which may be identical or different denote hydrogen methyl, ethyl or propyl, or
$R^1$ and $R^{1'}$ together denote —$CH_2$—$CH_2$—, —$CH_2$—$CH_2$—$CH_2$—$CH_2$— or —$CH_2$—$CH_2$—$CH_2$—$CH_2$—$CH_2$—;
$R^2$ and $R^{2'''}$ denote hydrogen;
$R^{2'}$ and $R^{2''}$ which may be identical or different denote a group selected from among hydrogen, methyl, $CF_3$, OH, methyloxy, benzyloxy or fluorine;
n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also particularly preferred are compounds of formula 1‴ wherein $R^1$ and $R^b$ may have the above-mentioned meanings and wherein
V denotes the double-bonded group O;
$R^1$ and $R^{1'}$ which may be identical or different, preferably identical, denote hydrogen, methyl, ethyl or propyl;
$R^2$, $R^{2''}$ and $R^{2'''}$ denote hydrogen;
$R^{2'}$ denotes hydrogen, OH, methyloxy or benzyloxy,
n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of exceptional importance according to the invention are the compounds of formula 1‴, wherein $R^a$ and $R^b$ may have the above-mentioned meanings and wherein
V denotes the double-bonded group O;
$R^1$ and $R^{1'}$ in each case simultaneously denote hydrogen, methyl, ethyl or propyl;
$R^2$, $R^{2''}$ and $R^{2'''}$ denote hydrogen;
$R^{2'}$ denotes hydrogen, OH or methyloxy,
n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of particular importance according to the invention are those compounds of formula 1‴ wherein $R^a$ and $R^b$ both represent methyl. These compounds may be represented by the formula 1.1‴

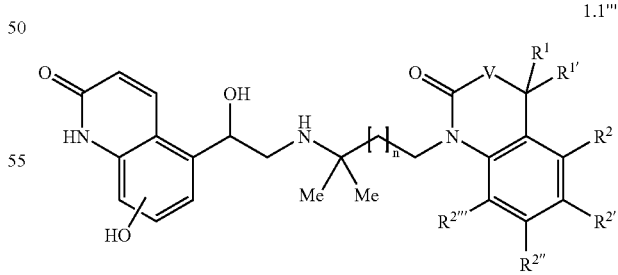

1.1‴ wherein the groups $R^1$, $R^{1'}$, $R^2$, $R^{2'}$, $R^{2''}$, $R^{2'''}$ and V may have the above-mentioned meanings.

Also of particular importance according to the invention are compounds of formula 1 wherein X denotes the group —$CMe_2$-O—. These compounds may be represented by the formula 1″″

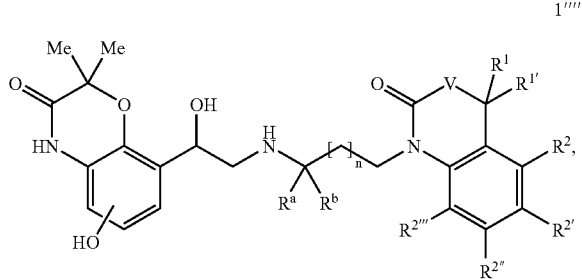

wherein the groups $R^a$, $R^b$, $R^1$, $R^{1'}$, $R^2$, $R^{2'}$, $R^{2''}$, $R^{2'''}$ and V are as hereinbefore defined.

Preferred are compounds of formula 1'''' wherein $R^a$ and $R^b$ may have the above-mentioned meanings and wherein V denotes a double-bonded group selected from among $CH_2$ and O, preferably O;

$R^1$ and $R^{1'}$ which may be identical or different, denote a group selected from among hydrogen, methyl, ethyl, propyl, cyclopropyl, or $R^1$ and $R^{1'}$ together denote —$CH_2$—$CH_2$—$CH_2$—$CH_2$— or —$CH_2$—$CH_2$—$CH_2$—$CH_2$—$CH_2$—;

$R^2$ and $R^{2'''}$ denote hydrogen;

$R^{2'}$ and $R^{2''}$ which may be identical or different, denote a group selected from among hydrogen, methyl, $CF_3$, OH, methyloxy, benzyloxy, COOH, $COOCH_3$ or fluorine;

n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Particularly preferred are compounds of formula 1'''' wherein $R^a$ and $R^b$ may have the above-mentioned meanings and wherein V denotes a double-bonded group selected from among $CH_2$ and O, preferably O;

$R^1$ and $R^{1'}$ which may be identical or different, denote hydrogen, methyl, ethyl or propyl or $R^1$ and $R^{1'}$ together denote —$CH_2$—$CH_2$—$CH_2$—$CH_2$—$CH_2$—;

$R^2$ and $R^{2'''}$ denote hydrogen;

$R^{2'}$ and $R^{2''}$ which may be identical or different, denote a group selected from among hydrogen, methyl, $CF_3$, OH, methyloxy, benzyloxy or fluorine;

n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also particularly preferred are the compounds of formula 1'''' wherein $R^a$ and $R^b$ may have the above-mentioned meanings and wherein V denotes the double-bonded group O;

$R^1$ and $R^{1'}$ which may be identical or different, preferably identical, denote hydrogen, methyl, ethyl or propyl;

$R^2$, $R^{2''}$ and $R^{2'''}$ denote hydrogen;

$R^{2'}$ denotes hydrogen, OH, methyloxy or benzyloxy, n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of exceptional importance according to the invention are the compounds of formula 1'''', wherein $R^a$ and $R^b$ may have the above-mentioned meanings and wherein V denotes the double-bonded group O;

$R^1$ and $R^{1'}$ in each case simultaneously denote hydrogen, methyl, ethyl or propyl;

$R^2$, $R^{2''}$ and $R^{2'''}$ denote hydrogen;

$R^{2'}$ denotes hydrogen, OH or methyloxy, n denotes 0, 1 or 2, preferably 1;

optionally in the form of the individual optical isomers, mixtures of the individual enantiomers or racemates, in the form of the free bases or the corresponding acid addition salts with pharmacologically acceptable acids.

Also of particular importance according to the invention are those compounds of formula 1'''' wherein $R^a$ and $R^b$ both represent methyl. These compounds may be represented by the formula 1.1''''

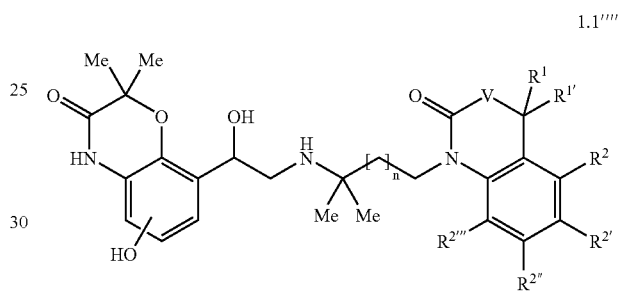

wherein the groups $R^1$, $R^{1'}$, $R^2$, $R^{2'}$, $R^{2''}$, $R^{2'''}$ and V may have the above-mentioned meanings.

Also of outstanding importance according to the invention are the compounds of formula 1 wherein $R^1$ and $R^{1'}$ in each case simultaneously denote hydrogen, methyl or ethyl, preferably methyl or ethyl, particularly preferably ethyl;

and the groups X, $R^2$, $R^{2'}$, $R^{2''}$, $R^{2'''}$, V and n may have one of the above-mentioned meanings, optionally in the form of the individual optical isomers, mixtures of the individual enantiomers or racemates, in the form of the free bases or the corresponding acid addition salts with pharmacologically acceptable acids.

Also of exceptional importance according to the invention are the compounds of formula 1, wherein n 1 and the groups X, $R^1$, $R^{1'}$, $R^2$, $R^{2'}$, $R^{2''}$, $R^{2'''}$ and V may have one of the above-mentioned meanings, optionally in the form of the individual optical isomers, mixtures of the individual enantiomers or racemates, in the form of the free bases or the corresponding acid addition salts with pharmacologically acceptable acids.

Particularly preferred compounds of general formula 1 are selected from among:

1-{3-[2-hydroxy-2-(6-hydroxy-3-oxo-3,4-dihydro-2H-benzo[1,4]oxazin-8)-yl-ethylamino]-3-methyl-butyl}-6-methoxy-4,4-dimethyl-1,4-dihydro-benzo[d][1,3]oxazin-2-one, 6-hydroxy-1-{3-[2-hydroxy-2-(6-hydroxy-3-oxo-3,4-dihydro-2H-benzo[1,4]oxazin-8-yl)-ethylamino]-3-methyl-butyl}-4,4-dimethyl-1,4-dihydro-benzo[d][1,3]oxazin-2-one, 4,4-diethyl-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[d][1,3]oxazin-2-one, 6-hydroxy-8-{1-hydroxy-2-[3-(3-hydroxy-4,4-dimethyl-1-oxo-3,4-dihydro-1H-isoquinolin-2-yl)-1,1-dimethyl-propylamino]-ethyl}-4H-benzo[1,4]oxazin-3-one, 1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[1,3]oxazin-2-one, 4-ethyl-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[1,3]oxazin-2-one, 8-{2-[1,1-dimethyl-3-(2-oxo-3,4-dihydro-2H-quinolin-1-yl)-propylamino]-1-hydroxy-ethyl}-6-hydroxy-4H-benzo[1,4]oxazin-3-one, 4,4-diethyl-1-{3-[2-hydroxy-2-(8-hydroxy-2-oxo-1,2-dihydro-quinolin-5-yl)-ethylamino]-3-methyl-butyl}-1,4-dihydro-benzo[1,3]oxazin-2-one, 4,4-diethyl-1-{3-[2-hydroxy-2-(6-hydroxy-2,2-dimethyl-3-oxo-3,4-dihydro-2H-benzo[1,4]oxazin-8-yl)-ethylamino]-3-methyl-butyl}-1,4-dihydro-benzo[d][1,3]oxazin-2-one, 4,4-diethyl-1-{3-[2-hydroxy-2-(6-hydroxy-2,2-dimethyl-3-oxo-3,4-dihydro-2H-benzo[1,4]oxazin-8-yl)-ethylamino]-3-methyl-butyl}-1,4-dihydro-benzo[d][1,3]oxazin-2-one, 4,4-diethyl-1-{3-[2-hydroxy-2-(7-hydroxy-2-oxo-1,2-dihydro-quinolin-5-yl)-ethylamino]-3-methyl-butyl}-1,4-dihydro-benzo[d][1,3]oxazin-2-one, 1-{3-[2-hydroxy-2-(6-hydroxy-3-oxo-3,4-dihydro-2H-benzo[1,4]oxazin-8-yl)-ethylamino]-3-methyl-butyl}-4,4-dipropyl-1,4-dihydro-benzo[d][1,3]oxazin-2-one, 1-{3-[2-hydroxy-2-(5-hydroxy-3-oxo-3,4-dihydro-2H-benzo[1,4]oxazin-8-yl)-ethylamino]-3-methyl-butyl}-4,4-dipropyl-1,4-dihydro-benzo[d][1,3]oxazin-2-one, 4,4-diethyl-7-fluoro-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[d][1,3]oxazin-2-one, 4,4-diethyl-1-{3-[2-hydroxy-2-(5-hydroxy-3-oxo-3,4-dihydro-2H-benzo[1,4]oxazin-8-yl)-ethylamino]-3-methyl-butyl}-8-methoxy-1,4-dihydro-benzo[d][1,3]oxazin-2-one, 1-(2-{1-[2-hydroxy-2-(5-hydroxy-3-oxo-3,4-dihydro-2H-benzo[1,4]oxazin-8-yl)-ethylamino]-cyclopropyl}-ethyl)-4,4-dimethyl-1,4-dihydro-benzo[d][1,3]oxazin-2-one, 1-(2-{1-[2-hydroxy-2-(6-hydroxy-3-oxo-3,4-dihydro-2H-benzo[1,4]oxazin-8-yl)-ethylamino]-cyclopropyl}-ethyl)-4,4-dimethyl-1,4-dihydro-benzo[d][1,3]oxazin-2-one, 1-{3-[2-hydroxy-2-(6-hydroxy-3-oxo-3,4-dihydro-2H-benzo[1,4]oxazin-8-yl)-ethylamino]-3-methyl-butyl}-spiro(cyclohexane-1,4'-2H-3',1'-benzoxazin)-2'-one, 1-{3-[2-hydroxy-2-(5-hydroxy-3-oxo-3,4-dihydro-2H-benzo[1,4]oxazin-8-yl)-ethylamino]-3-methyl-butyl}-spiro(cyclohexane-1,4'-2H-3',1'-benzoxazin)-2'-one;

4,4-dimethyl-1-{3-[2-hydroxy-2-(6-hydroxy-3-oxo-3,4-dihydro-2H-benzo[1,4]oxazin-8-yl)-ethylamino]-propyl}-1,4-dihydro-benzo[d][1,3]oxazin-2-one;

4,4-dimethyl-1-{3-[2-hydroxy-2-(5-hydroxy-3-oxo-3,4-dihydro-2H-benzo[1,4]oxazin-8-yl)-ethylamino]-propyl}-1,4-dihydro-benzo[d][1,3]oxazin-2-one, optionally in the form of the individual optical isomers, mixtures of the individual enantiomers or racemates, in the form of the free bases or the corresponding acid addition salts with pharmacologically acceptable acids The OH— group may be configured in three different positions in the compounds of formula 1 defined hereinbefore. The preferred isomers may be represented by the following general formulae 1a and 1b,

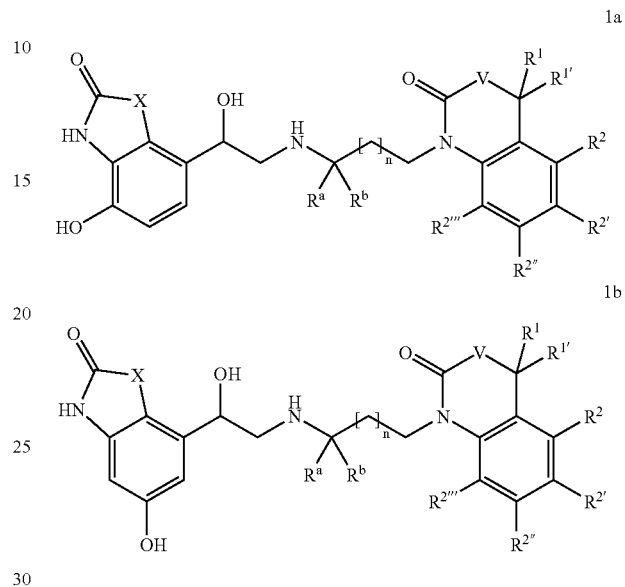

wherein the groups X, $R^a$, $R^b$, $R^1$, $R^{1'}$, $R^2$, $R^{2'}$, $R^{2''}$, $R^{2'''}$, V and n may have the above-mentioned meanings.

Particularly preferred compounds are particularly also those of general formula 1.1'-b

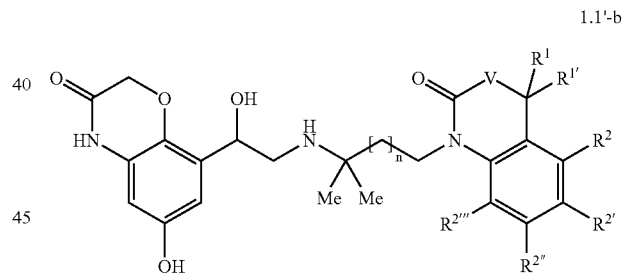

wherein the groups $R^1$, $R^{1'}$, $R^2$, $R^{2'}$, $R^{2''}$, $R^{2'''}$ and V may have the above-mentioned meanings.

Particularly preferred compounds are particularly also those of general formula 1.1"-b

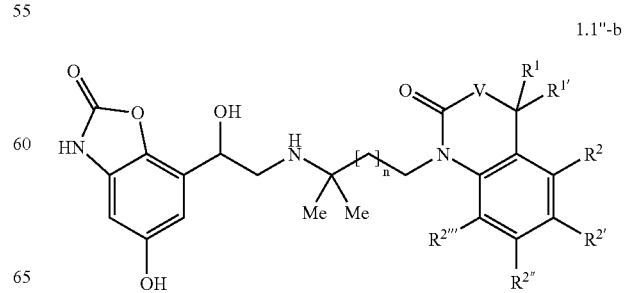

wherein the groups $R^1$, $R^{1'}$, $R^2$, $R^{2'}$, $R^{2''}$, $R^{2'''}$ and V may have the above-mentioned meanings.

Particularly preferred compounds are particularly also those of general formula 1.1'''-a

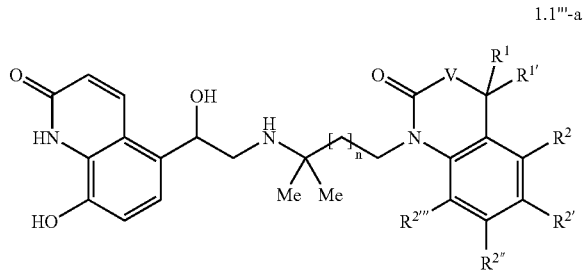

1.1'''-a wherein the groups $R^1$, $R^{1'}$, $R^2$, $R^{2'}$, $R^{2''}$, $R^{2'''}$ and V may have the above-mentioned meanings.

Particularly preferred compounds are particularly also those of general formula 1.1''''-b

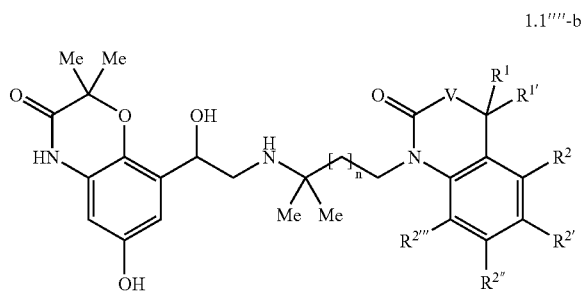

1.1''''-b wherein the groups $R^1$, $R^{1'}$, $R^2$, $R^{2'}$, $R^{2''}$, $R^{2'''}$ and V may have the above-mentioned meanings.

The compounds of formula 1 may optionally be used in the form of the individual optical isomers, mixtures of the individual enantiomers or racemates. They are particularly preferably used in the form of the enantiomerically pure compounds, while the compounds of formula 1 wherein the asymmetric carbon centre "—CH(OH)—" benzylic to the phenyl ring is in the R configuration [sic]. The particularly preferred R-enantiomers of the compounds of general formula 1 may be represented by general formula R-1,

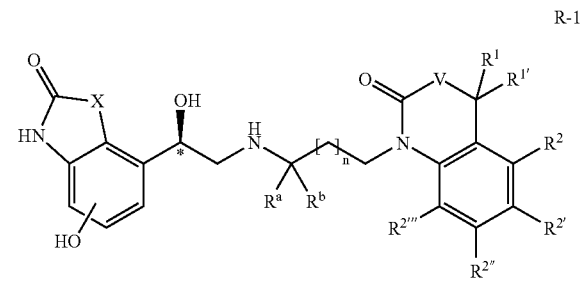

R-1 wherein the groups X, $R^a$, $R^b$, $R^1$, $R^{1'}$, $R^2$, $R^{2'}$, $R^{2''}$, $R^{2'''}$, V and n may have the above-mentioned meanings.

By acid addition salts with pharmacologically acceptable acids are meant, for example, the salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Halogen within the scope of the present invention denotes fluorine, chlorine, bromine or iodine. Unless stated otherwise, fluorine and bromine are the preferred halogens, while fluorine is generally preferred.

Unless otherwise stated, the alkyl groups (alkyl) are straight-chained or branched alkyl groups having 1 to 6, preferably 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Examples of alkylene groups (alkylene), unless otherwise stated, are branched and unbranched alkylene groups with 1 to 6, preferably 1 to 4 carbon atoms. The following are mentioned by way of example: methylene, ethylene, propylene or butylene. Unless stated otherwise, the definitions propylene and butylene include all the possible isomeric forms of the groups in question.

Examples of cycloalkyl groups (cycloalkyl), unless otherwise stated, are cyclic alkyl groups with 3 to 6. The following are mentioned by way of example: cyclopropyl, cyclobutanyl, cyclopentyl or cyclohexyl.

Examples of alkyloxy groups (O-alkyl), unless otherwise stated, are branched and unbranched alkyl groups with 1 to 6, preferably 1 to 4 carbon atoms, linked via an oxygen atom. The following are mentioned by way of example: methyloxy, ethyloxy, propyloxy or butyloxy. In some cases the abbreviations —OMe, —OEt, —Oprop or —OBu are used to denote the groups methyloxy, ethyloxy, propyloxy or butyloxy. Unless stated otherwise, the definitions propyloxy and butyloxy include all the possible isomeric forms of the groups in question. Thus, for example, propyloxy includes n-propyloxy and iso-propyloxy, butyloxy includes iso-butyloxy, sec-butyloxy and tert-butyloxy etc. In some cases within the scope of the present invention the term alkoxy may be used instead of the term alkyloxy. The groups methyloxy, ethyloxy, propyloxy or also butyloxy may optionally also be referred to as methoxy, ethoxy, propoxy or butoxy.

Examples of halogenoalkylene groups, unless otherwise stated, are branched and unbranched alkyl groups with 1 to 6 carbon atoms, wherein one or more hydrogen atoms are replaced by halogen atoms, preferably by fluorine. The following are mentioned, for example: $CHF_2$, $CF_3$, $CH_2CF_3$, $CF_2CF_3$.

Suitable aryl groups, unless otherwise stated, are aromatic ring systems with 6 to 10 carbon atoms. Preferred aryl groups are phenyl and naphthyl, while phenyl is particularly preferred according to the invention.

The term arylalkylene groups, unless otherwise stated, refers to the above-mentioned aryl groups which are linked via branched and unbranched alkyl groups with 1 to 4 carbon atoms. Examples include benzyl, phenylethyl, naphthylmethyl, naphthylethyl. The bridging alkyl groups are also referred to, within the scope of the present invention, as alkylene bridges.

The term aryloxy groups (O-aryl), unless otherwise stated, refers to aryl groups with 6 to 10 carbon atoms which are linked via an oxygen bridge. Preferred groups in this context include for example phenyloxy or naphthyloxy, which may optionally also be referred to as phenoxy or naphthoxy within the scope of the present invention.

The term arylalkylenoxy groups (arylalkylene-O—), unless otherwise stated, refers to aryl groups which are linked via branched and unbranched alkyloxy groups with 1 to 4 carbon atoms. Examples include benzyloxy, phenylethyloxy, naphthylmethyloxy, naphthylethyloxy.

The compounds according to the invention may be prepared analogously to methods already known in the art. Suitable methods of preparation are known for example from EP 43 940 or from WO 01/83462, to which reference is hereby made in its entirety.

The examples of synthesis described below serve to illustrate new compounds according to the invention in more detail. However, they are intended only as examples of procedures to illustrate the invention without restricting it to the subject matter described in an exemplifying capacity hereinafter.

EXAMPLE 1

1-{3-[2-hydroxy-2-(6-hydroxy-3-oxo-3,4-dihydro-2H-benzo[1,4]oxazin-8-yl)-ethylamino]-3-methyl-butyl}-6-methoxy-4,4-dimethyl-1,4-dihydro-benzo[d][1,3]oxazin-2-one

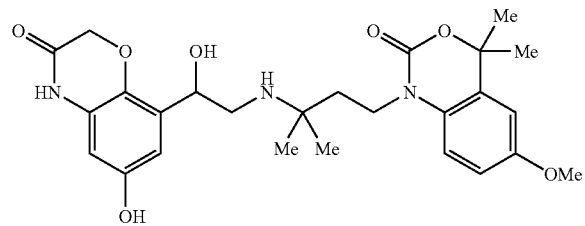

a) ethyl (2-acetyl-4-methoxy-phenyl)-carbamate 65.1 g (0.6 mol) ethyl chloroformate are added dropwise to a solution of 82.5 g (0.5 mol) 2-amino-5-methoxyacetophenone in 400 mL pyridine while cooling, so that the temperature does not exceed 10–15° C. Then the reaction mixture is stirred for 2 h at ambient temperature and then poured onto ice. The precipitate formed is suction filtered, washed with water and recrystallised from isopropanol.

Yield: 102 g (86%); m.p.=97–100° C.

b) 6-methoxy-4,4-dimethyl-1,4-dihydro-benzo[1,3]oxazin-2-one 47.4 g (0.2 mol) ethyl (2-acetyl-4-methoxy-phenyl)-carbamate, dissolved in 275 mL THF, are added dropwise to a solution of 0.5 mol methylmagnesium iodide in 200 mL diethyl ether while cooling so that the temperature does not exceed 0° C. The mixture is stirred for 30 minutes at ambient temperature and then for 2 hours at reflux temperature. The reaction mixture is poured onto ice and combined with ammonium chloride. After the organic phase has been separated off it is repeatedly extracted with ethyl acetate. The organic phases are combined, washed with water, dried with sodium sulphate and evaporated down. The residue is dissolved in methanol and the solution is evaporated down and then combined with water. The precipitate formed is separated off, washed with water and recrystallised from toluene. Yield: 31.1 g (75%); m.p.=178–180° C.

c) 1-(3-amino-3-methyl-butyl)-6-methoxy-4,4-dimethyl-1,4-dihydro-benzo[1,3]oxazin-2-one A solution of 31 g (0.15 mol) 6-methoxy-4,4-dimethyl-1,4-dihydro-benzo[1,3]oxazin-2-on in 120 mL HMPT is added dropwise at 65–70° C. to 7.2 g sodium hydride (55–60%) in 30 mL HMPT. After the release of hydrogen has ended the mixture is stirred for another 20 minutes and then cooled to ambient temperature. At this temperature 37.7 g (0.18 mol) (3-chloro-1,1-dimethyl-propyl)-benzylidene-amine, dissolved in 40 mL HMPT, are added. After 3 hours stirring at 100° C. the reaction mixture is poured onto ice poured and extracted with ethyl acetate. The organic phases are washed with water, dried with sodium sulphate and evaporated down. The residue is dissolved in 1 N hydrochloric acid with heating and after cooling extracted with diethyl ether. The aqueous phase is made alkaline with sodium hydroxide solution and extracted with ethyl acetate. Then the organic phase is dried with sodium sulphate and freed from solvent. The product is isolated from the residue in the form of its hydrochloride, after dissolving in acetonitrile and adding ethereal hydrochloric acid. Yield: 34.3 g (70%).

d) 1-{3-[2-(6-benzyloxy-3-oxo-3,4-dihydro-2H-benzo[1,4]oxazin-8-yl)-2-hydroxy-ethylamino]-3-methyl-butyl}-6-methoxy-4,4-dimethyl-1,4-dihydro-benzo[1,3]oxazin-2-one 357 mg (1 mmol) of 6-benzyloxy-8-(2-ethoxy-2-hydroxy-acetyl)-4H-benzo[1,4]oxazin-3-one and 292 mg (1 mmol) 1-(3-amino-3-methyl-butyl)-6-methoxy-4,4-dimethyl-1,4-dihydro-benzo[1,3]oxazin-2-one are suspended in 5 mL ethanol and heated to 70° C. The solution obtained is stirred for one hour at 70° C. and then cooled to ambient temperature. After the addition of 113 mg (3 mmol) sodium borohydride the mixture is stirred for 3 hours at ambient temperature, combined with 0.7 mL saturated potassium carbonate solution and stirred for a further 30 minutes. It is filtered through aluminium oxide (basic), washed repeatedly with methylene chloride/methanol 15:1 and evaporated down. The crude product thus obtained is purified by chromatography (methylene chloride with methanol/ammonia gradient (9:1)). Beige solid. Yield: 340 mg (58%); mass spectrometry: [M+H]$^+$=590.

e) 1-{3-[2-hydroxy-2-(6-hydroxy-3-oxo-3,4-dihydro-2H-benzo[1,4]oxazin-8-yl)-ethylamino]-3-methyl-butyl}-6-methoxy-4,4-dimethyl-1,4-dihydro-benzo[d][1,3]oxazin-2-one 340 mg (0.58 mmol) 1-{3-[2-(6-benzyloxy-3-oxo-3,4-dihydro-2H-benzo[1,4]oxazin-8-yl)-2-hydroxy-ethylamino]-3-methyl-butyl}-6-methoxy-4,4-dimethyl-1,4-dihydro-benzo[1,3]oxazin-2-one are dissolved in 10 mL methanol and hydrogenated with palladium on charcoal as catalyst at 1 bar hydrogen pressure. Then the catalyst is filtered off and the filtrate is evaporated down. Beige solid. Yield: 273 mg (95%); mass spectrometry: [M+H]$^+$=500; Rf value=0.33 (methylene chloride:methanol:ammonia=9:1:0.1).

EXAMPLE 2

6-hydroxy-1-{3-[2-hydroxy-2-(6-hydroxy-3-oxo-3,4-dihydro-2H-benzo[1,4]oxazin-8-yl)-ethylamino]-3-methyl-butyl}-4,4-dimethyl-1,4-dihydro-benzo[d][1,3]oxazin-2-one

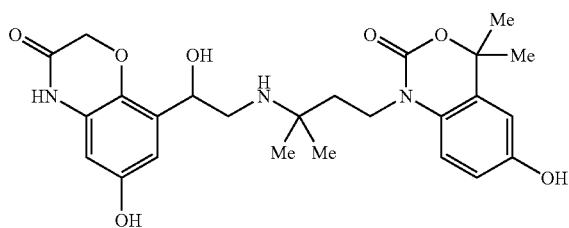

a) 6-benzyloxy-4,4-dimethyl-1,4-dihydro-benzo[1,3]oxazin-2-one

Prepared analogously to the method described for Example 1b) from 15.7 g (50 mmol) ethyl (2-acetyl-4-benzyloxy-phenyl)-carbamate and 125 mmol methylmagnesium iodide.

Yield: 10.8 g (76%); m.p.=134° C.

b) 1-(3-amino-3-methyl-butyl)-6-benzyloxy-4,4-dimethyl-1,4-dihydro-benzo[1,3]oxazin-2-one Prepared analogously to the method described for Example 1c) from 10.5 g (37 mmol) 6-benzyloxy-4,4-dimethyl-1,4-dihydro-benzo[1,3]oxazin-2-one and 9.3 g (44 mmol) (3-chloro-1,1-dimethyl-propyl)-benzylideneamine. Yield: 10.9 g (73%); m.p.=233° C. (hydrochloride).

c) 6-hydroxy-1-{3-[2-hydroxy-2-(6-hydroxy-3-oxo-3,4-dihydro-2H-benzo[1,4]oxazin-8-yl)-ethylamino]-3-methyl-butyl}-4,4-dimethyl-1,4-dihydro-benzo[1,3]oxazin-2-one The reaction of 357 mg (1 mmol) 6-benzyloxy-8-(2-ethoxy-2-hydroxy-acetyl)-4H-benzo[1,4]oxazin-3-one and 368 mg (1 mmol) 1-(3-amino-3-methyl-butyl)-6-benzyloxy-4,4-dimethyl-1,4-dihydro-benzo[1,3]oxazin-2-one analogously to the methods described for Example 1 yields the compound in the form of a beige solid. Yield 355 mg (73%); mass spectrometry: [M+H]$^+$=486.

EXAMPLE 3

4,4-diethyl-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[d][1,3]oxazin-2-one

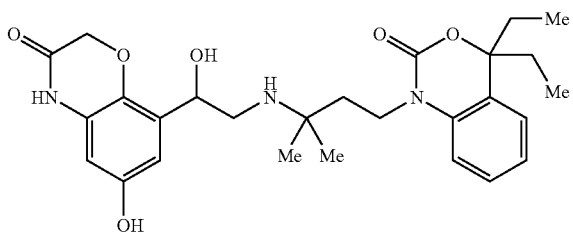

a) 4,4-diethyl-1,4-dihydro-benzo[1,3]oxazin-2-one

Obtained from the reaction of 67 g (0.3 mol) methyl 2-ethoxycarbonylamino-benzoate and 1.14 mol ethylmagnesium iodide analogously to the method described for Example 1b). Yield: 48.5 g (79%); m.p.=160–162° C.

b) 1-(3-amino-3-methyl-butyl)-4,4-diethyl-1,4-dihydro-benzo[1,3]oxazin-2-one

Prepared from 47.5 g (0.23 mol) 4,4-diethyl-1,4-dihydro-benzo[1,3]oxazin-2-one and 57.5 g (0.27 mol) (3-chloro-1,1-dimethyl-propyl)-benzylideneamine according to the method described for Example 1c). Yield: 38.1 g (50%); m.p.=208–210° C. (hydrochloride).

c) 4,4-diethyl-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[d][1,3]oxazin-2-one 357 mg (1 mmol) 6-benzyloxy-8-(2-ethoxy-2-hydroxy-acetyl)-4H-benzo[1,4]oxazin-3-one and 290 mg (1 mmol) 1-(3-amino-3-methyl-butyl)-4,4-diethyl-1,4-dihydro-benzo[1,3]oxazin-2-one are reacted analogously to the methods described for Example 1. After subsequent debenzylation a beige solid is obtained. Yield: 367 mg (74%); mass spectrometry: [M+H]$^+$=498.

EXAMPLE 4

1-{3-[2-hydroxy-2-(6-hydroxy-3-oxo-3,4-dihydro-2H-benzo[1,4]oxazin-8-yl)-ethylamino]-3-methyl-butyl}-4,4-dimethyl-1,4-dihydro-benzo[d][1,3]oxazin-2-one

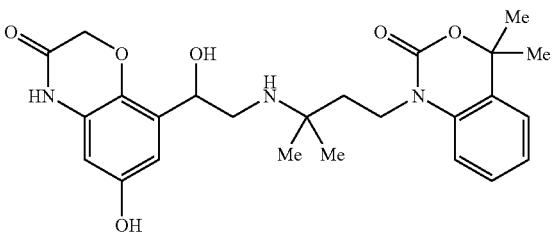

a) 4,4-dimethyl-1,4-dihydro-benzo[1,3]oxazin-2-one 112 g (1.13 mol) phosgene are piped into 500 mL THF. Then a solution of 52 g (0.34 mol) 2-(2-amino-phenyl)-propan-2-ol, prepared from 2-aminoacetophenone and methylmagnesium iodide, in 300 mL THF is added. The reaction mixture is left to stand overnight, evaporated down and combined with 500 ml pyridine. After the pyridine has been distilled off water is added and the mixture is extracted with diethyl ether. The organic phases are washed successively with 2 N hydrochloric acid, sodium hydroxide solution and water, dried with sodium sulphate and evaporated down. The residue remaining (46 g) is further reacted directly without any more purification.

m.p. (toluene/petroleum ether)=109–110° C.

b) 1-(3-amino-3-methyl-butyl)-4,4-dimethyl-1,4-dihydro-benzo[1,3 ]oxazin-2-one

Obtained from 43 g (0.24 mol) 4,4-dimethyl-1,4-dihydro-benzo[1,3]oxazin-2-one and 54 g (0.26 mol) (3-chloro-1,1-dimethyl-propyl)-benzylideneamine analogously to the method described for Example 1c). Yield 41 g (57%); m.p. (after recrystallisation from ethanol)=262° C. (hydrochloride).

c) 1-{3-[2-hydroxy-2-(6-hydroxy-3-oxo-3,4-dihydro-2H-benzo[1,4]oxazin-8-yl)-ethylamino]-3-methyl-butyl}-4,4-dimethyl-1,4-dihydro-benzo[d][1,3]oxazin-2-one 357 mg (1 mmol) 6-benzyloxy-8-(2-ethoxy-2-hydroxy-acetyl)-4H-benzo[1,4]oxazin-3-one and 262 mg (1 mmol) 1-(3-amino-3-methyl-butyl)-4,4-dimethyl-1,4-dihydrobenzo[1,3]oxazin-2-one are reacted in the manner described for Example 1. After subsequent hydrogenation a beige solid is isolated. Yield: 285 mg (61%); mass spectrometry [M+H]$^+$=470.

EXAMPLE 5

1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[1,3]oxazin-2-one

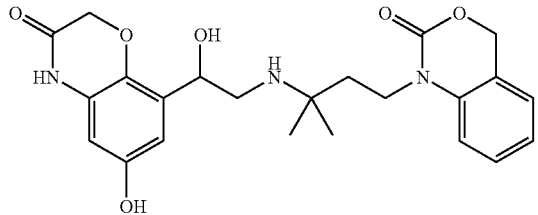

a) 1-(3-amino-3-methyl-butyl)-1,4-dihydro-benzo[1,3]oxazin-2-one 2.70 g (18 mmol) 1,4-dihydro-benzo[1,3]oxazin-2-one and 4.35 g (21 mmol) (3-chloro-1,1-dimethyl-propyl)-(1-phenyl-methylidene)-amine are reacted in the manner described for Example 6a). For working up the reaction mixture is poured onto ice water and extracted with ethyl acetate. The organic phases are washed with water, dried with sodium sulphate and evaporated down. The residue is combined with 25 mL 2 N hydrochloric acid and heated to 70° C. After cooling to ambient temperature the mixture is extracted with diethyl ether. The aqueous phase is evaporated down and combined with acetonitrile. The precipitate formed is suction filtered and washed with acetonitrile and diethyl ether. Yield: 2.65 g (54%, hydrochloride); melting range: 220° C. (decomposition).

b) 1-{3-[2-(6-benzyloxy-3-oxo-3,4-dihydro-2H-benzo[1,4]oxazin-8-yl)-2-hydroxy-ethylamino]-3-methyl-butyl}-1,4-dihydro-benzo[1,3]oxazin-2-one 357 mg (1 mmol) 6-benzyloxy-8-(2-ethoxy-2-hydroxy-acetyl)-4H-benzo[1,4]oxazin-3-one and 234 mg (1 mmol) 1-(3-amino-3-methyl-butyl)-1,4-dihydro-benzo[1,3]oxazin-2-one in 5 mL tetrahydrofuran are stirred for 15 minutes at 60° C. The mixture is cooled to 0° C. and 1.5 mL of a 2 molar solution of lithium borohydride in tetrahydrofuran are added dropwise under an argon atmosphere. The mixture is stirred for 15 min at 0° C., combined with 10 mL dichloromethane and 3 mL water, stirred for another hour and then filtered through kieselguhr. The mixture is eluted with dichloromethane and the solvents are distilled off. The residue is purified by preparative HPLC (reverse phase, acetonitrile/water gradient with 0.1% trifluoroacetic acid).

Yield: 196 mg (30%, trifluoroacetate); mass spectroscopy: [M]$^+$=532.

c) 1-{3-[2-(6-benzyloxy-3-oxo-3,4-dihydro-2H-benzo[1,4]oxazin-8-yl)-2-hydroxy-ethylamino]-3-methyl-butyl}-1,4-dihydro-benzo[1,3]oxazin-2-one 196 mg (0.3 mmol) 1-{3-[2-(6-benzyloxy-3-oxo-3,4-dihydro-2H-benzo[1,4]oxazin-8-yl)-2-hydroxy-ethylamino]-3-methyl-butyl}-1,4-dihydro-benzo[1,3]oxazin-2-one are dissolved in 5 ethanol and hydrogenated with palladium on charcoal (10%) as catalyst at 3 bar and ambient temperature. The catalyst is separated off and the crude product is recrystallised from acetonitrile/diethyl ether.

Yield: 48 mg (29%, trifluorethyl acetate); mass spectroscopy: [M+H]$^+$=442.

EXAMPLE 6

4-ethyl-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[1,3]oxazin-2-one

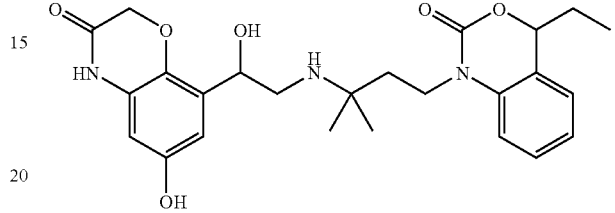

a) 1-(3-amino-3-methyl-butyl)-4-ethyl-1,4-dihydro-benzo[1,4]oxazine

A solution of 17.7 g (0.10 mol) 4-ethyl-1,4-dihydro-benzo[1,3]oxazin-2-one in 85 mL HMPT is combined with 4.8 g sodium hydride (55–60%) and slowly heated to 60° C. After the development of hydrogen has ended the mixture is stirred for another 30 min at 80° C. and then cooled to ambient temperature. 25 g (0.12 mol) (3-chloro-1,1-dimethyl-propyl)-(1-phenyl-methylidene)-amine, dissolved in 25 mL HMPT, are added and the mixture is stirred for three hours at 100° C. The reaction mixture is cooled, poured onto ice water and extracted with ethyl acetate. The combined organic phases are washed with water, dried with sodium sulphate and evaporated down. The residue is heated to 60° C. together with 240 mL 1N hydrochloric acid and after cooling extracted with diethyl ether. The aqueous phase is made alkaline with conc. sodium hydroxide solution and extracted with ethyl acetate. The combined organic phases are dried with sodium sulphate and evaporated down. The residue is dissolved in ethyl acetate with heating, combined with an equimolar amount of maleic acid and slowly cooled. The precipitate formed is suction filtered, washed with ethyl acetate and dried. Yield: 26.1 g (69%, maleate); melting range: 134° C.

b) 1-{3-[2-(6-benzyloxy-3-oxo-3,4-dihydro-2H-benzo[1,4]oxazin-8-yl)-2-hydroxy-ethylamino]-3-methyl-butyl}-4-ethyl-1,4-dihydro-benzo[1,3]oxazin-2-one 357 mg (1 mmol) 6-benzyloxy-8-(2-ethoxy-2-hydroxy-acetyl)-4H-benzo[1,4]oxazin-3-one and 530 mg (1 mmol) 1-(3-amino-3-methyl-butyl)-4-ethyl-1,4-dihydro-benzo[1,4]oxazine are reacted and worked up analogously to the method described in 5b).

Yield: 308 mg (46%, trifluoroacetate); mass spectroscopy: [M]$^+$=560.

c) 4-ethyl-1-{1,3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[1,3]oxazin-2-one 308 mg (0.46 mmol) 1-{3-[2-(6-benzyloxy-3-oxo-3,4-dihydro-2H-benzo[1,4]oxazin-8-yl)-2-hydroxy-ethylamino]-3-methyl-butyl}-4-ethyl-1,4-dihydro-benzo[1,3]oxazin-2-one are hydrogenated with palladium on charcoal (10%) as catalyst at ambient temperature and under 3 bar hydrogen pressure. The catalyst is separated off, the filtrate evaporated down and the residue is chromatographed (reverse phase; acetonitrile/water gradient).

Yield: 14 mg (5%, trifluoroacetate); mass spectroscopy: [M]$^+$=470.

EXAMPLE 7

8-{2-[1,1-dimethyl-3-(2-oxo-3,4-dihydro-2H-quinolin-1-yl)-propylamino]-1-hydroxy-ethyl}-6-hydroxy-4H-benzo[1,4]oxazin-3-one

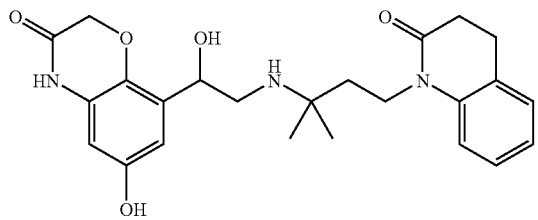

a) 1-(3-amino-3-methyl-butyl)-3,4-dihydro-quinolin-2-one

Prepared analogously to the method described for Example 6a) from 15.7 g (107 mmol) 3,4-dihydro-quinolin-2-one and 24.9 g (119 mmol) (3-chloro-1,1-dimethyl-propyl)-(1-phenyl-methylidene)-amine. Unlike in the method mentioned above the product is precipitated not as the maleate but as the hydrochloride.

Yield: 6.9 g (24%, hydrochloride); melting range: 200–203° C.

b) 8-{2-[1,1-dimethyl-3-(2-oxo-3,4-dihydro-2H-quinolin-1-yl)-propylamino]-1-hydroxy-ethyl}-6-hydroxy-4H-benzo[1,4]oxazin-3-one Prepared from 357 mg (1 mmol) 6-benzyloxy-8-(2-ethoxy-2-hydroxy-acetyl)-4H-benzo[1,4]oxazin-3-one and 232 mg (1 mmol) 1-(3-amino-3-methyl-butyl)-3,4-dihydro-quinolin-2-one analogously to the method described for Example 5c). The final purification of the product is carried out by preparative HPLC (reverse phase, acetonitrile/water gradient with 0.1% trifluoroacetic acid).

Yield: 94 mg (17%, trifluoroacetate); mass spectroscopy: [M]$^+$=440.

EXAMPLE 8

4,4-diethyl-1-{3-[2-hydroxy-2-(8-hydroxy-2-oxo-1,2-dihydro-quinolin-5-yl)-ethylamino]-3-methyl-butyl}-1,4-dihydro-benzo[1,3]oxazin-2-one

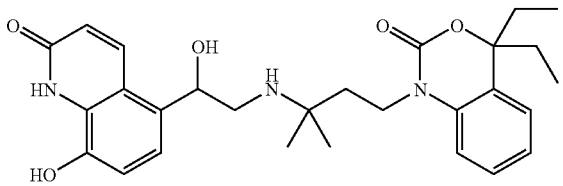

a) 1-{3-[2-(8-benzyloxy-2-oxo-1,2-dihydro-quinolin-5-yl)-2-hydroxy-ethylamino]-3-methyl-butyl}-4,4-diethyl-1,4-dihydro-benzo[1,3]oxazin-2-one 400 mg (1.4 mmol) of 8-benzyloxy-5-oxiranyl-quinolin-2-one and 436 mg (1.5 mmol) 1-(3-amino-3-methyl-butyl)-4,4-diethyl-1,4-dihydro-benzo[1,3]oxazin-2-one in 5 mL of n-butanol are stirred for 6 hours at 140° C. The solvent is distilled off and the residue is purified by chromatography (reverse phase; acetonitrile/water gradient). Beige solid.

Yield: 160 mg (20%); mass spectroscopy: [M]$^+$=584.

b) 4,4-diethyl-1-{3-[2-hydroxy-2-(8-hydroxy-2-oxo-1,2-dihydro-quinolin-5-yl)-ethylamino]-3-methyl-butyl}-1,4-dihydro-benzo[1,3]oxazin-2-one 160 mg (0.3 mmol) 1-{3-[2-(8-benzyloxy-2-oxo-1,2-dihydro-quinolin-5-yl)-2-hydroxy-ethylamino]-3-methyl-butyl}-4,4-diethyl-1,4-dihydro-benzo[1,3]oxazin-2-one are dissolved in 5 mL methanol and hydrogenated in the presence of palladium on charcoal (10%). Yield: 49 mg (34%); mass spectroscopy: [M]$^+$=494.

EXAMPLE 9

4,4-diethyl-1-{3-[2-hydroxy-2-(6-hydroxy-2,2-dimethyl-3-oxo-3,4-dihydro-2H-benzo[1,4]oxazin-8-yl)-ethylamino]-3-methyl-butyl}-1 4-dihydro-benzo[d][1,3]oxazin-2-one

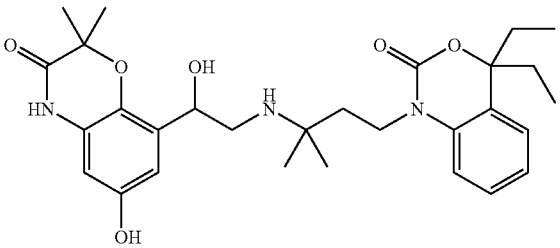

a) N-(3-acetyl-5-benzyloxy-2-hydroxy-3phenyl)-2-bromo-2-methyl-propionamide 4.64 g (25 mmol) 2-bromo-2-methyl-propionyl chloride are added dropwise to a solution of 5.15 g (20 mmol) 1-(3-amino-5-benzyloxy-2-hydroxy-phenyl)-ethanone in 20 mL pyridine at 5–20° C. After the addition has ended the mixture is stirred for 15 minutes, combined with ice water and 100 mL ethyl acetate and acidified with conc. hydrochloric acid. The organic phase is separated off, washed with water and dried with sodium sulphate. After the solvent has been distilled off the residue is crystallised from a diethyl ether/petroleum ether mixture. Yield: 6.8 g (84%); melting range: 88–90° C.

b) 8-acetyl-6-benzyloxy-2,2-dimethyl-4H-benzo[1,4]oxazin-3-one 6.60 g (16.2 mmol) N-(3-acetyl-5-benzyloxy-2-hydroxy-phenyl)-2-bromo-2-methyl-propionamide and 2.76 g (20 mmol) potassium carbonate are stirred for 1 hour in 70 mL acetonitrile at reflux temperature. The solid is suction filtered, the filtrate is evaporated down and the residue is combined with 30 mL ethyl acetate. After fresh filtration and distilling off the solvent the crude product is crystallised from a little methanol.

Yield: 1.00 g (19%); mass spectroscopy [M+H]$^+$=326; melting range=148–150° C.

c) 6-benzyloxy-8-(2-ethoxy-2-hydroxy-acetyl)-2,2-dimethyl-benzo[1,4]oxazin-3-one 50.12 g (154 mmol) 8-acetyl-6-benzyloxy-2,2-dimethyl-benzo[1,4]oxazin-3-one are reacted with selenium dioxide as oxidising agent and activated charcoal in refluxing dioxane and some water. After cooling, the solid is filtered off and washed with dioxane. The filtrate is evaporated down and the residue is dissolved in 550 mL ethanol and refluxed for 30 minutes. It is filtered and the mother liquor is cooled to −18° C., during which time a solid is precipitated which is suction filtered. After recrystallisation from ethanol the product is obtained in the form of a beige solid. Yield: 8.95 g (15%).

d) 1-{3-[2-(6-benzyloxy-2,2-dimethyl-3-oxo-3,4-dihydro-2H-benzo[1,4]oxazin-8-yl)-2-hydroxy-ethylamino]-3-methyl-butyl}-4,4-diethyl-1,4-dihydro-benzo[d][1,3]oxazin-2-one Prepared from 406 mg (1 mmol) 6-benzyloxy-8-(2-ethoxy-2-hydroxy-acetyl)-2,2-dimethyl-benzo[1,4]oxazin-3-one and 290 mg (1 mmol) 1-(3-amino-3-methyl-butyl)-4,4-diethyl-1,4-dihydro-benzo[1,3]oxazin-2-one analogously to the method described for Example 5b). The target compound is purified by chromatography with silica gel on a short column (dichloromethane/methanol gradient). White solid.
Yield: 145 mg (24%); mass spectroscopy [M+H]$^+$=616.

e) 4,4-diethyl-1-{3-[2-hydroxy-2-(6-hydroxy-2,2-dimethyl-3-oxo-3,4-dihydro-2H-benzo[1,4]oxazin-8-yl)-ethylamino]-3-methyl-butyl}-1,4-dihydro-benzo[d][1,3]oxazin-2-one 130 mg (0.21 mmol) 1-{3-[2-(6-benzyloxy-2,2-dimethyl-3-oxo-3,4-dihydro-2H-benzo[1,4]oxazin-8-yl)-2-hydroxy-ethylamino]-3-methyl-butyl}-4,4-diethyl-1,4-dihydro-benzo[d][1,3]oxazin-2-one are dissolved in 5 mL methanol and hydrogenated in the presence of palladium on charcoal (10%) at ambient temperature. The catalyst is suction filtered, the filtrate is evaporated down and the residue is purified by chromatography (Reverse phase; acetonitrile/water gradient). White solid.
Yield: 41 mg (37%); mass spectroscopy [M+H]$^+$=526.

EXAMPLE 10

4,4-diethyl-1-{3-[2-hydroxy-2-(5-hydroxy-2-oxo-2,3-dihydro-benzooxazol-7-yl)-ethylamino]-3-methyl-butyl}-1,4-dihydro-benzo[d][1,3]oxazin-2-one

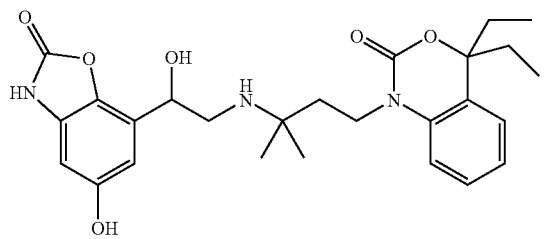

a) 7-acetyl-5-benzyloxy-3H-benzooxazol-2-one 51.1 mL (97.04 mmol) of a phosgene solution (20% by weight in toluene) are added at 0° C. to a solution of 22.7 g (88.22 mmol) 1-(3-amino-5-benzyloxy-2-hydroxy-phenyl)-ethanone in toluene (200 mL). Then 30.7 mL (220.6 mmol) triethylamine are added dropwise such that the temperature does not exceed 5° C. After 1 h stirring at ambient temperature a further 4.6 mL phosgene solution and 12 mL triethylamine are added at 0° C. The mixture is stirred for 1 h at ambient temperature, diluted with dichloromethane and combined with saturated aqueous ammonium chloride solution (500 mL) and 2 N aqueous hydrochloric acid (10 mL). After the aqueous phase has been separated off it is exhaustively extracted with dichloromethane. The combined organic phases are washed with water and saturated aqueous sodium chloride solution, dried with sodium sulphate and evaporated down i. vac., during which time a beige solid is precipitated. The precipitate is filtered off, washed with a little toluene and dried at 50° C. i. vac.
Yield: 18.5 g (74%); $R_f$=0.19 (silica gel, toluene/acetone 95:10); ESI-MS: [M+H]$^+$=284.

b) 5-benzyloxy-7-(2-ethoxy-2-hydroxy-acetyl)-3H-benzooxazol-2-one 14.4 mL (127.1 mmol) HBr (48% in water) are added to a solution of 12.0 g (42.4 mmol) 7-acetyl-5-benzyloxy-3H-benzooxazol-2-one in DMSO (60 mL). The mixture is stirred for 6 h at 60° C. under a gentle nitrogen current, poured onto 600 mL ice water and stirred for 20 min. The precipitate formed is filtered off and washed with ice water and cold water/ethyl acetate solution (1:1). The precipitate is dissolved in 300 mL ethanol and 100 mL ethyl acetate and evaporated down i. vac. The process is repeated with 500 mL toluene and then with 500 mL ethanol. The residue is then dissolved in 250 mL ethanol and refluxed for 1 h. After 30 mL ethanol have been distilled off the mixture is cooled to ambient temperature and then to 0° C. The precipitate formed is filtered off, washed with 80 mL ice-cold ethanol and 200 mL ether and dried at 50° C. i. vac.
Yield: 6.5 g (45%); $R_f$=0.23 (silica gel, dichloromethane/MeOH 25:2); ESI-MS: [M+H—CO$_2$Et]$^+$=270.

c) 1-{3-[2-(5-benzyloxy-2-oxo-2,3-dihydro-benzooxazol-7-yl)-2-hydroxy-ethylamino]-3-methyl-butyl}-4,4-diethyl-1,4-dihydro-benzo[d][1,3]oxazin-2-one Obtained from 343 mg (1 mmol) 5-benzyloxy-7-(2-ethoxy-2-hydroxy-acetyl)-3H-benzooxazol-2-one and 290 mg (1 mmol) 1-(3-amino-3-methyl-butyl)-4,4-diethyl-1,4-dihydro-benzo[1,3]oxazin-2-one according to the method described for Example 5b). White solid. Yield: 160 mg (28%); mass spectroscopy [M−H]$^+$=572.

d) 4,4-diethyl-1-{3-[2-hydroxy-2-(5-hydroxy-2-oxo-2,3-dihydro-benzooxazol-7-yl)-ethylamino]-3-methyl-butyl}-1,4-dihydro-benzo[d][1,3]oxazin-2-one 150 mg (0.26 mmol) 1-{3-[2-(5-benzyloxy-2-oxo-2,3-dihydro-benzooxazol-7-yl)-2-hydroxy-ethylamino]-3-methyl-butyl}-4,4-diethyl-1,4-dihydro-benzo[d][1,3]oxazin-2-one are dissolved in 5 mL methanol and hydrogenated with palladium on charcoal as catalyst for 3 hours at ambient temperature. The catalyst is separated off and the filtrate is evaporated down. Beige solid. Yield: 116 mg (92%); mass spectroscopy [M−H]$^+$=484.
HPLC method (method A): Symmetry C18 (Waters); 3.5 μm; 4.6×150 mm; Column temperature: 20° C.; gradient acetonitrile/phosphate buffer (pH 7) 20:80→80:20 in 30 min., flow: 1.0 mL/min; detection at 220 and 254 nm.

EXAMPLE 11

4,4-diethyl-1-{3-[2-hydroxy-2-(7-hydroxy-2-oxo-1 2-dihydro-quinolin-5-yl)-ethylamino]-3-methyl-butyl}-1,4-dihydro-benzo[d][1,3]oxazin-2-one

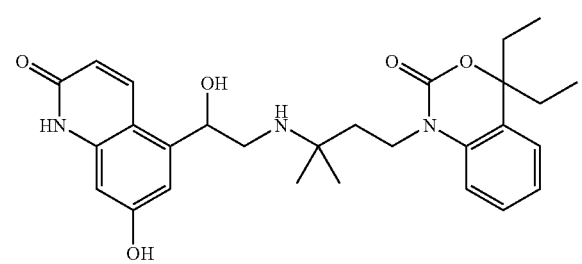

a) 2-acetyl-4-benzyloxy-6-nitro-phenyl trifluoromethane-sulphonate

Triethylamine (92.7 mL, 0.660 mol) is added to a solution of 1-(5-benzyloxy-2-hydroxy-3-nitro-phenyl)-ethanone (90.0 g, 0.313 mol) in abs. dichloromethane (940 mL) at −10 ° C. within 10 min. A solution of trifluoromethane-sulphonic anhydride (65 mL, 0.394 mol) in abs. dichloromethane (40 mL) is added to this red solution within 15 min. and the resulting mixture is stirred for a further 5 min. at −5° C. The brown solution is washed with saturated aqueous ammonium chloride (400mL) and saturated aqueous NaCl (400mL) and the phases are separated. Drying with sodium sulphate and evaporation i. vac. yields the crude product as an oil which becomes solid when left to stand. The crude product is dissolved in ether (150 mL), the solution is combined with hexane (800 mL) and the precipitate formed is filtered off. The solid is stirred with ether/hexane (80/20, 100 mL), filtered off and dried in the oven at 40° C. Yield: 118 g (90%); ESI-MS: [M+H]$^+$=420.

b) methyl 3-(2-acetyl-4-benzyloxy-6-nitrophenyl)-acrylate 100 g of molecular sieve (4 Å), tris(dibenzylideneacetone)dipalladium (5.88 g, 6.42 mmol), tri-tert-butylphosphonium-tetrafluoroborate (3.50 g, 12.06 mmol), dicyclohexylmethylamine (81.2 mL, 0.371 mol), dried tetrabutylammonium iodide (105.8 g, 0.286 mol) and methyl acrylate (32.6 mL, 0.362 mol) are added to a solution of 2-acetyl-4-benzyloxy-6-nitro-phenyl trifluoromethane-sulphonate (100.0 g, 0.238 mol) in dioxane (360 mL) under a nitrogen atmosphere. The reaction mixture is stirred for 2 hours at 80° C., diluted with ether (2 L) and combined with 500 g silica gel. The suspension is stirred for 10 min., filtered and the silica gel is washed several times with ether (4×600 mL). The combined organic phases are washed with 1 M aqueous hydrochloric acid (300 mL), sodium bicarbonate solution and sodium chloride solution, dried with sodium sulphate and evaporated down. The oily crude product is recrystallised from hot ethanol (0.75 L). The precipitate is filtered off, washed with ethanol (2×50 mL) and dried at 40 ° C.

Yield: 32.2 g (38%); mass spectroscopy: [M+H]$^+$=356.

c) 5-acetyl-7-benzyloxy-3,4-dihydro-1H-quinolin-2-one

A suspension of methyl 3-(2-acetyl-4-benzyloxy-6-nitrophenyl)-acrylate (5.0 g, 14.07 mmol) in ethanol (100 mL) is hydrogenated with Raney nickel (3 g) at ambient temperature and 4 bar hydrogen pressure. After 6 hours more Raney nickel (2 g) is added and the mixture is hydrogenated for a further 2 hours. The catalyst is separated off and the filtrate is combined with 2 M aqueous hydrochloric acid (15 mL). The product that crystallises out is filtered off and dried.

Yield: 1.0 g (24%); mass spectroscopy: [M+H]$^+$=296.

d) 5-acetyl-7-benzyloxy-1H-quinolin-2-one

DDQ (15.0 g, 66.08 mmol) is added to a suspension of 5-acetyl-7-benzyloxy-3,4-dihydro-1H-quinolin-2-one (13.0 g, 44.02 mmol) in dioxane (130 mL) and the mixture is refluxed for 30 minutes. The reaction mixture is cooled to ambient temperature and stirred for a further 2 hours. The precipitate formed is filtered off, washed with dioxane (2×20 mL) and dissolved in dichloromethane/methanol (9:1, 600 mL). The organic phase is washed with sodium bicarbonate solution (2×100 mL), dried with sodium sulphate and evaporated down. The residue is stirred with methanol, the precipitate formed is filtered off and dried. Yield: 8.3 g (64%); mass spectroscopy: [M+H]$^+$=294.

e) 7-benzyloxy-5-(2-chloroacetyl)-1H-quinolin-2-one 5-acetyl-7-benzyloxy-1H-quinolin-2-one (7.0 g, 23.86 mmol) is dissolved in a mixture of 1,2-dichloroethane (147 mL), glacial acetic acid (43 mL) and water (7 mL) and combined with N-benzyl-trimethylammonium-dichloriodate (19.0 g, 54.58 mmol). The mixture is stirred for 4.5 hours at 65° C., then diluted with sodium bicarbonate solution and 5% sodium bisulphite solution and stirred for 5 minutes. The precipitate formed is filtered off, washed with water (2×20 mL) and dried in the oven. Yield: 6.0 g (77%); mass spectroscopy: [M+H]$^+$=328.

f) 7-benzyloxy-5-oxiranyl-1H-quinolin-2-one

Lithium borohydride (434 mg, 19.93 mmol) is added to a suspension of 7-benzyloxy-5-(2-chloroacetyl)-1H-quinolin-2-one (6 g, 18.31 mmol) in THF (150 mL) at 0–5 ° C. and the mixture is stirred for 30 minutes. 2.5 N sodium hydroxide solution (43 mL, 107.50 mmol) is added and the mixture is stirred for 2 hours at 5–10 ° C. and for 2.5 hours at ambient temperature. Then the reaction mixture is slowly combined with glacial acetic acid (6.5 mL) followed by semi-saturated sodium chloride solution (100 mL) and stirred for a further 5 minutes. The precipitate formed is filtered off and the aqueous phase is extracted with ethyl acetate/THF (1/1.5× 100 mL). The solid filtered off and the organic phases are combined, dried with sodium sulphate and evaporated down. The crude product is stirred with methanol (30 mL) and the precipitate is filtered off and dried at ambient temperature. Yield: 4.8 g (89%); mass spectroscopy: [M+H]$^+$=294.

g) 1-{1,3-[2-(7-benzyloxy-2-oxo-1,2-dihydro-quinolin-5-yl)-2-hydroxy-ethylamino]-3-methyl-butyl}-4,4-diethyl-1,4-dihydro-benzo[d][1,3]oxazin-2-one A suspension of 7-benzyloxy-5-oxiranyl-1H-quinolin-2-one (112 mg, 0.382 mmol) and 1-(3-amino-3-methyl-butyl)-4,4-diethyl-1,4-dihydro-benzo[d][1,3]oxazin-2-one (220 mg, 0.758 mmol) in isopropanol (1.0 mL) is heated in the microwave for 1 h to 135 ° C. The mixture is diluted with EtOAc (10 mL) and washed with 0.5 M aqueous tartaric acid solution, whereupon half the product is precipitated. The phases are separated and the aqueous suspension is combined with MeOH until a clear solution is obtained again. The aqueous phase is extracted with dichloromethane and the combined org. phases are dried with sodium sulphate and evaporated down i. vac. The residue is stirred with EtOAc and the precipitate is filtered off and dried i. vac.

Yield: 152 mg (68%); HPLC-MS: R$_t$=14.8 min. (method A).

h) 4,4-diethyl-1-{3-[2-hydroxy-2-(7-hydroxy-2-oxo-1,2-dihydro-quinolin-5-yl)-ethylamino]-3-methyl-butyl}-1,4-dihydro-benzo[d][1,3]oxazin-2-one A suspension of 1-{3-[2-(7-benzyloxy-2-oxo-1,2-dihydro-quinolin-5-yl)-2-hydroxy-ethylamino]-3-methyl-butyl}-4,4-diethyl-1,4-dihydro-benzo[d][1,3]oxazin-2-one (152 mg, 0.338 mmol) and Pd/C (10%) (40 mg) in MeOH (12 mL) is hydrogenated at RT and 1 bar hydrogen pressure for 4 h. The catalyst is filtered off through Celite and washed with MeOH (5 mL). The org. phase is evaporated down, the residue is triturated with EtOAc and the precipitate formed is filtered off and dried. i. vac.

Yield: 76 mg (46%); R$_f$=0.3 (silica gel, dichloromethane/MeOH/saturated. aqueous ammonia 90:10:0.5); ESI-MS: [M+H]$^+$=494.

Specific starting compounds are needed for the examples of synthesis that follow. Their preparation is described hereinafter.

Intermediate Product 1: 1-(3-amino-3-methyl-butyl)-4,4-dilpropyl-1,4-dihydro-benzo[d][1,3]oxazin-2-one hydrochloride

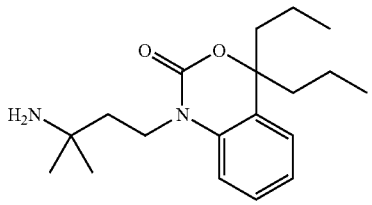

a) 4-(2-amino-phenyl)-heptan-4-ol 90.0 mL (180.00 mmol) of propylmagnesium chloride (2 M in ether) are added dropwise within 30 min. to a solution of 7.00 mL (54.04 mmol) methyl anthranilate in abs. THF (70 mL) at 0° C. The mixture is stirred for 1 h at RT and then combined with 100 mL 3 M aqueous ammonium chloride solution and EtOAc. The phases are separated and the aqueous phase is exhaustively extracted with EtOAc. The combined org. phases are washed with aqueous $KHCO_3$ and sat. aqueous NaCl and dried with sodium sulphate. The crude product is used in the next reaction step without any further purification.

Yield: 6.70 g (60%).

b) tert-butyl {3-[2-(1-hydroxy-1-propyl-butyl)-phenylamino]-1,1-dimethyl-propyl}-carbamate 1.40 g (22.27 mmol) sodium cyanoborohydride are added to a solution of 3.10 g (14.05 mmol) 4-(2-amino-phenyl)-heptan-4-ol and 3.60 g (17.88 mmol) tert-butyl (1,1-dimethyl-3-oxo-propyl)-carbamate in MeOH (40 mL) and AcOH (6 mL). The mixture is stirred for 16 h at RT, diluted with EtOAc and washed with 0.5 M aqueous $KHSO_4$ and saturated. aqueous NaCl , dried with sodium sulphate and evaporated down i. vac. The crude product is used in the next reaction step without any further purification.

Yield: 6.00 g (quantitative yield).

c) tert-butyl [1,1-dimethyl-3-(2-oxo-4,4-dipropyl-4H-benzo[d][1,3]oxazin-1-yl)-propyl]-carbamate 8.85 mL (16.81 mmol) phosgene solution (20 wt. % in toluene) are slowly added dropwise at 0° C. to a solution of 6.00 g (15.28 mmol) tert-butyl{3-[2-(1-hydroxy-1-propyl-butyl)-phenylamino]-1,1-dimethyl-propyl}-carbamate and 5.32 mL (38.21 mmol) triethylamine in abs. THF (80 mL). The mixture is stirred for 2 h at RT, diluted with EtOAc, combined with ice and made basic with sat. aqueous ammonia solution. The aqueous phase is exhaustively extracted with EtOAc and the combined org. phases are washed with saturated aqueous NaCl, dried with sodium sulphate and evaporated down i. vac. After column chromatography (silica gel, cyclohexane/EtOAc 6:1) the product is obtained as a yellow oil. Yield: 4.57 g (71%).

d) 1-(3-amino-3-methyl-butyl)-4,4-dipropyl-1,4-dihydro-benzo[d][1,3]oxazin-2-one hydrochloride A solution of 4.20 g (10.03 mmol) tert-butyl [1,1-dimethyl-3-(2-oxo-4,4-dipropyl-4H-benzo[d][1,3]oxazin-1-yl)-propyl]-carbamate in 35 mL formic acid is stirred for 24 h at RT and then poured onto ice. The aqueous phase is made basic with sat. aqueous ammonia solution and exhaustively extracted with EtOAc. The combined org. extracts are washed with sat. aqueous NaCl , dried with sodium sulphate and evaporated down i. vac. The residue is taken up in EtOAc (50 mL) and combined with 4 mL HCl solution (sat. in EtOAc). The solution is concentrated by evaporation and twice combined with a little EtOH and evaporated down i. vac. Trituration of the residue with diisopropylether yields the product as a hygroscopic hydrochloride salt. Yield: 2.60 g (73%).

Intermediate Product 2: 1-(3-amino-3-methyl-butyl)-4,4-diethyl-7-fluoro-1,4-dihydro-benzo[d][1,3]oxazin-2-one

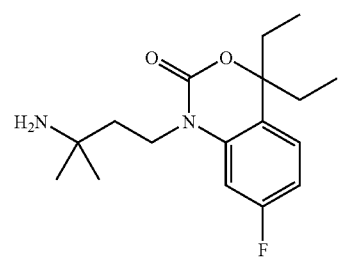

a) 3-(2-amino-4-fluoro-phenyl)-pentan-3-ol

The product is obtained analogously to intermediate product 1a by reacting methyl 2-amino-4-fluoro-benzoate and ethylmagnesium bromide in dichloromethane at −78° C.→RT. Yield: 4.1 g (99%).

b) tert-butyl{3-[2-(1-ethyl-1-hydroxy-propyl)-5-fluoro-phenylamino]-1,1-dimethyl-propyl}-carbamate The product is obtained analogously to intermediate product 1b starting from 3-(2-amino-4-fluoro-phenyl)-pentan-3-ol and tert-butyl (1,1-dimethyl-3-oxo-propyl)-carbamate. The crude product is purified by column chromatography (silica gel, dichloromethane/MeOH 100:0→98:2). Yield: 7.70 g (99%).

c) tert-butyl [3-(4,4-diethyl-7-fluoro-2-oxo-4H-benzo[d][1,3]oxazin-1-yl)-1,1-dimethyl-propyl]-carbamate The product is obtained analogously to intermediate product 1c starting from tert-butyl {3-[2-(1-ethyl-1-hydroxy-propyl)-5-fluoro-phenylamino]-1,1-dimethyl-propyl}-carbamate. Yield: 4.20 g (51%).

d) 1-(3-amino-3-methyl-butyl)-4,4-diethyl-7-fluoro-1,4-dihydro-benzo[d][1,3]oxazin-2-one The product is obtained analogously to intermediate product 1d starting from tert-butyl [3-(4,4-diethyl-7-fluoro-2-oxo-4H-benzo[d][1,3]oxazin-1-yl)-1,1-dimethyl-propyl]-carbamate as the free base. Yield: 2.90 g (96%); ESI-MS: $[M+H]^+=309$.

Intermediate Product 3: 1-(3-amino-3-methyl-butyl)-4,4-diethyl-8-methoxy-1,4-dihydro-benzo[d][1,3]oxazin-2-one

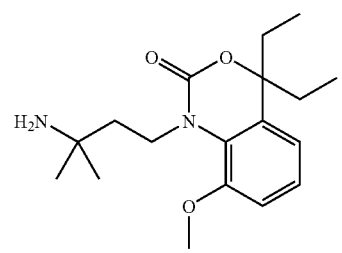

a) 3-(2-amino-3-methoxy-phenyl)-pentan-3-ol

The product is obtained analogously to intermediate product 1a by reacting methyl 2-amino-3-methoxy-benzoate and ethylmagnesium bromide in dichloromethane at −78 °C. → RT.

Yield: 5.20 g (92%); HPLC-MS: $R_t$=12.85 min. (method A); ESI-MS: $[M+H]^+$=210.

b) tert-butyl {3-[2-(1-ethyl-1-hydroxy-propyl)-6-methoxy-phenylamino]-1,1-dimethyl-propyl}-carbamate The product is obtained analogously to intermediate product 1b starting from 3-(2-amino-3-methoxy-phenyl)-pentan-3-ol and tert-butyl (1,1-dimethyl-3-oxo-propyl)-carbamate. The crude product is purified by column chromatography (silica gel, cyclohexane/EtOAc 4:1). Yield: 4.60 g (47%).

c) tert-butyl [3-(4,4-diethyl-8-methoxy-2-oxo-4H-benzo[d][1,3]oxazin-1-yl)-1,1-dimethyl-propyl]-carbamate The product is obtained analogously to intermediate product 1c starting from tert-butyl {3-[2-(1-ethyl-1-hydroxy-propyl)-6-methoxy-phenylamino]-1,1-dimethyl-propyl}-carbamate. Yield: 4.60 g (94%).

d) 1-(3-amino-3-methyl-butyl)-4,4-diethyl-8-methoxy-14-dihydro-benzo[d][1,3]oxazin-2-one The product is prepared as the free base analogously to intermediate product 1d starting from tert-butyl [3-(4,4-diethyl-8-methoxy-2-oxo-4H-benzo[d][1,3]oxazin-1-yl)-1,1-dimethyl-propyl]-carbamate. Yield: 3.00 g (93%); ESI-MS: $[M+H]^+$=321.

Intermediate Product 4: 1-(3-amino-3-methyl-butyl)-spiro(cyclohexane-1,4'-2H-3'1'-benzoxazin)-2'-one

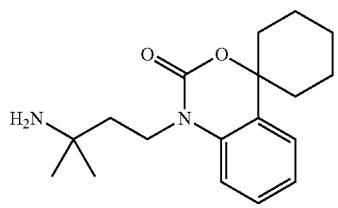

a) 1-(2-nitro-phenyl)-cyclohexanol 40.16 mL (80.32 mmol) phenylmagnesium chloride (2 M in THF) are added dropwise at −50° C. to a solution of 20.0 g (80.32 mmol) 2-nitro-iodobenzene in abs. THF (150 mL) under a nitrogen atmosphere. After stirring for 15 min. 9.98 mL (96.30 mmol) cyclohexanone are added quickly. The mixture is heated to RT and stirred for a further 2 h. Sat. aqueous ammonium chloride solution is added and the aqueous phase is exhaustively extracted with EtOAc. The combined org. extracts are washed with sat. aqueous NaCl solution, dried with sodium sulphate and evaporated down in vacuo. After column chromatography (silica gel, hexane/EtOAc 20:1) the product is obtained as a brownish oil. Yield: 5.20 g (29%); $R_f$=0.26 (silica gel, hexane/EtOAc 10:1); ESI-MS: $[M+H-H_2O]^+$=204.

b) 1-(2-amino-phenyl)-cyclohexanol

A suspension of 5.20 g (16.45 mmol) 1-(2-nitro-phenyl)-cyclohexanol and 500 mg Raney nickel in EtOH (70 mL) is hydrogenated at RT and under 3 bar hydrogen pressure for 4 h. The catalyst is filtered off through Celite and the filtrate is evaporated down in vacuo. The residue is recrystallised from hexane. Yield: 1.53 g (49%); $R_f$=0.38 (silica gel, hexane/EtOAc 4:1); ESI-MS: $[M+H-H_2O]^+$=174.

c) tert-butyl {3-[2-(1-hydroxy-cyclohexyl)-phenylamino]-1,1-dimethyl-propyl}-carbamate The product is prepared analogously to intermediate product 1b starting from 1-(2-amino-phenyl)-cyclohexanol and tert-butyl (1,1-dimethyl-3-oxo-propyl)-carbamate. After column chromatography (silica gel, hexane/EtOAc 7:1) the product is obtained as a colourless oil. Yield: 2.65 g (66%); $R_f$=0.50 (silica gel, hexane/EtOAc 4:1).

d) tert-butyl [3-(spiro(cyclohexane-1,4'-2H-3'1'-benzoxazin)-2'-oxo-1-yl)-1,1-dimethyl-propyl]-carbamate The product is prepared analogously to intermediate product 1c starting from tert-butyl {3-[2-(1-hydroxy-cyclohexyl)-phenylamino]-1,1-dimethyl-propyl}-carbamate.

Yield: 2.60 g (92%); $R_f$=0.38 (silica gel, hexane/EtOAc 4:1).

e) 1-(3-amino-3-methyl-butyl)-spiro(cyclohexane-1,4'-2H-3'1'-benzoxazin)-2'-one

The product is prepared analogously to intermediate product 1 d starting from tert-butyl [3-(spiro(cyclohexane-1,4'-2H-3',1'-benzoxazin)-2 '-oxo-1-yl)-1,1-dimethyl-propyl]-carbamate. Yield: 1.80 g (92%); $R_f$=0.10 (silica gel, dichloromethane/MeOH/sat. aqueous ammonia 95:5:0.5); ESI-MS: $[M+H]^+$=303.

EXAMPLE 12

1-{3-[2-hydroxy-2-(6-hydroxy-3-oxo-3,4-dihydro-2H-benzo[1,4]oxazin-8-yl)-ethylamino]-3-methyl-butyl}-4,4-dipropyl-1,4-dihydro-benzo[d][1,3]oxazin-2-one

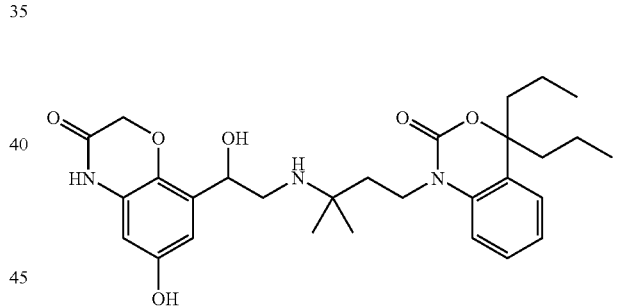

a) 1-{3-[2-(6-benzyloxy-3-oxo-3,4-dihydro-2H-benzo[1,4]oxazin-8-yl)-2-hydroxy-ethylamino]-3-methyl-butyl}-4,4-dipropyl-1,4-dihydro-benzo[d][1,3]oxazin-2-one 86 μL (0.619 mmol) triethylamine are added to a solution of 200 mg (0.564 mmol) 1-(3-amino-3-methyl-butyl)-4,4-dipropyl-1,4-dihydro-benzo[d][1,3]oxazin-2-one hydrochloride in abs. THF (5 mL) at RT under a nitrogen atmosphere and the mixture is stirred for 30 min. 200 mg (0.560 mmol) 6-benzyloxy-8-(2-ethoxy-2-hydroxy-acetyl)-4H-benzo[1,4]oxazin-3-one are added and the mixture is stirred for another 2 h at RT. The mixture is cooled to 10° C., combined with 51 mg (2.34 mmol) lithium borohydride, heated to RT and stirred for 1 h at RT. It is again cooled to 10° C. and slowly combined with 15 mL water and 20 mL dichloromethane. The phases are separated and the aqueous phase is extracted with dichloromethane. The combined org. phases are dried with sodium sulphate and evaporated down in vacuo. The residue is dissolved in EtOAc (8 mL) and acidified to pH 2 by the addition of HCl solution (sat. in EtOAc). The precipitate formed is filtered off, washed with EtOAc and dried in vacuo.

Yield: 270 mg (74%; hydrochloride), HPLC-MS: $R_t$=18.7 min. (method A).

b)  1-{3-[2-hydroxy-2-(6-hydroxy-3-oxo-3,4-dihydro-2H-benzo[1,4]oxazin-8-yl)-ethylamino]-3-methyl-butyl}-4,4-dipropyl-1,4-dihydro-benzo[d][1,3]oxazin-2-one A suspension of 270 mg (0.438 mmol) 1-{3-[2-(6-benzyloxy-3-oxo-3,4-dihydro-2H-benzo[1,4]oxazin-8-yl)-2-hydroxy-ethylamino]-3-methyl-butyl}-4,4-dipropyl-1,4-dihydro-benzo[d][1,3]oxazin-2-one and 27 mg Pd/C (10%) in MeOH (8 mL) is hydrogenated at RT and 1 bar hydrogen pressure for 3 h. The catalyst is filtered off through Celite and washed with MeOH (5 mL) and the filtrate is concentrated by evaporation in vacuo. The residue is dissolved in EtOAc/dichloromethane (1:1, 10 mL), acidified to pH 2 by the addition of HCl solution (sat. in EtOAc) and concentrated by evaporation in vacuo. The residue is triturated with ether, filtered and dried in vacuo.

Yield: 80 mg (33%; hydrochloride), HPLC-MS: $R_t$=12.8 min. (method A), ESI-MS: [M+H]$^+$=526.

EXAMPLE 13

1-{3-[2-hydroxy-2-(5-hydroxy-3-oxo-3,4-dihydro-2H-benzo[1,4 4]oxazin-8-yl)-ethylamino]-3-methyl-butyl}-4,4-dipropyl-1,4-dihydro-benzo[d][1,3]oxazin-2-one

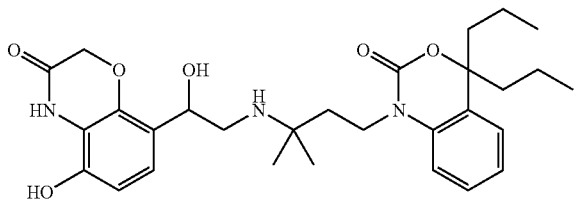

a)  1-{3-[2-(5-benzyloxy-3-oxo-3,4-dihydro-2H-benzo[1,4]oxazin-8-yl)-2-hydroxy-ethylamino]-3-methyl-butyl}-4,4-dipropyl-1,4-dihydro-benzo[d][1,3]oxazin-2-one The product is prepared analogously to Example 12a starting from 5-benzyloxy-8-(2,2-dihydroxy-acetyl)-4H-benzo[1,4]oxazin-3-one and 1-(3-amino-3-methyl-butyl)-4,4-dipropyl-1,4-dihydro-benzo[d][1,3]oxazin-2-one hydrochloride. The crude product is dissolved in EtOAc, washed with 5% aqueous NaOH solution and purified by column chromatography (silica gel, dichloromethane/MeOH 98:2→90:10).

Yield: 170 mg (49%); HPLC-MS: $R_t$=18.9 min. (method A).

b)  1-{3-[2-hydroxy-2-(5-hydroxy-3-oxo-3,4-dihydro-2H-benzo[1,4]oxazin-8-yl)-ethylamino]-3-methyl-butyl}-4,4-dipropyl-1,4-dihydro-benzo[d][1,3]oxazin-2-one The product is prepared analogously to Example 12b starting from 1-{3-[2-(5-benzyloxy-3-oxo-3,4-dihydro-2H-benzo[1,4]oxazin-8-yl)-2-hydroxy-ethylamino]-3-methyl-butyl}-4,4-dipropyl-1,4-dihydro-benzo[d][1,3]oxazin-2-one. Yield: 30 mg (19%, hydrochloride); HPLC-MS: $R_t$=13.0 min. (method A), ESI-MS: [M+H]$^+$=526.

EXAMPLE 14

4,4-diethyl-7-fluoro-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[d][1,3]oxazin-2-one

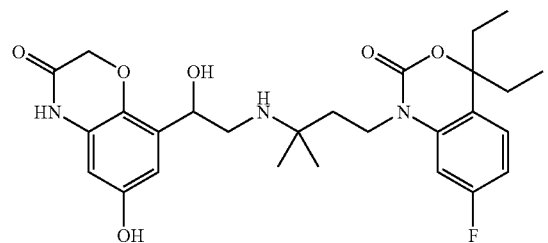

a)  1-{3-[2-(6-benzyloxy-3-oxo-3,4-dihydro-2H-benzo[1,4]oxazin-8-yl)-2-hydroxy-ethylamino]-3-methyl-butyl}-4,4-diethyl-7-fluoro-1,4-dihydro-benzo[d][1,3]oxazin-2-one A solution of 232 mg (0.649 mmol) 6-benzyloxy-8-(2-ethoxy-2-hydroxy-acetyl)-4H-benzo[1,4]oxazin-3-one and 200 mg (0.649 mmol) 1-(3-amino-3-methyl-butyl)-4,4-diethyl-7-fluoro-1,4-dihydro-benzo[d][1,3]oxazin-2-one in abs. THF (5 mL) is stirred for 2.5 h at RT. The mixture is cooled to 5° C., combined with 60 mg (2.755 mmol) lithium borohydride, heated to RT and stirred for 1 h. The mixture is again cooled to 5° C. and slowly diluted with 15 ml water and 20 mL dichloromethane. The phases are separated and the aqueous phase is extracted with dichloromethane. The combined org. phases are dried with sodium sulphate and concentrated by evaporation in vacuo. The residue is purified by column chromatography (silica gel, dichloromethane/MeOH 95:5).

Yield: 257 mg (65%); HPLC-MS: $R_t$=16.5 min. (method A).

b)  4,4-diethyl-7-fluoro-1-{3-[2-hydroxy-2-(6-hydroxy-3-oxo-3,4-dihydro-2H-benzo[1,4]oxazin-8-yl)-ethylamino]-3-methyl-butyl}-1,4-dihydro-benzo[d][1,3]oxazin-2-one The product is prepared analogously to Example 12b starting from 1-{3-[2-(6-benzyloxy-3-oxo-3,4-dihydro-2H-benzo[1,4]oxazin-8-yl)-2-hydroxy-ethylamino]-3-methyl-butyl}-4,4-diethyl-7-fluoro-1,4-dihydro-benzo[d][1,3]oxazin-2-one. Yield: 170 mg (78%; hydrochloride); HPLC-MS: $R_t$=10.6 min. (method A); ESI-MS: [M+H]$^+$=516.

EXAMPLE 15

4,4-diethyl-1-{3-[2-hydroxy-2-(5-hydroxy-3-oxo-3,4-dihydro-2H-benzo[1,4]oxazin-8-yl)-ethylamino]-3-methyl-butyl}-8-methoxy-1,4-dihydro-benzo[d][1,3]oxazin-2-one

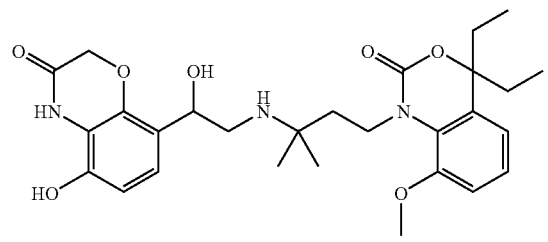

a) 1-{3-[2-(5-benzyloxy-3-oxo-3,4-dihydro-2H-benzo[1,4] oxazin-8-yl)-2-hydroxy-ethylamino]-3-methyl-butyl}-4,4-diethyl-8-methoxy-1,4-dihydro-benzo[d][1,3]oxazin-2-one The product is prepared analogously to Example 14a starting from 5-benzyloxy-8-(2,2-dihydroxy-acetyl)-4H-benzo[1,4]oxazin-3-one and 1-(3-amino-3-methyl-butyl)-4,4-diethyl-8-methoxy-1,4-dihydro-benzo[d][1,3]oxazin-2-one. The crude product is purified by column chromatography (silica gel, dichloromethane/MeOH 95:5).

Yield: 70 mg (18%); HPLC-MS: $R_t$=16.5 min. (method A).

b) 4,4-diethyl-1-{3-[2-hydroxy-2-(5-hydroxy-3-oxo-3,4-dihydro-2H-benzo[1,4]oxazin-8-yl)-ethylamino]-3-methyl-butyl}-8-methoxy-1,4-dihydro-benzo[d][1,3]oxazin-2-one The product is obtained analogously to Example 12b starting from 1-{3-[2-(5-benzyloxy-3-oxo-3,4-dihydro-2H-benzo[1,4]oxazin-8-yl)-2-hydroxy-ethylamino]-3-methyl-butyl}-4,4-diethyl-8-methoxy-1,4-dihydro-benzo[d][1,3]oxazin-2-one.

Yield: 40 mg (62%); HPLC-MS: $R_t$=13.3 min. (method A); ESI-MS: [M+H]$^+$=528.

EXAMPLE 16

1-(2-{1-[2-hydroxy-2-(5-hydroxy-3-oxo-3,4-dihydro-2H-benzo[1,4]oxazin-8-yl)-ethylamino]-cyclopropyl}-ethyl)-4,4-dimethyl-1,4-dihydro-benzo[d][1,3]oxazin-2-one

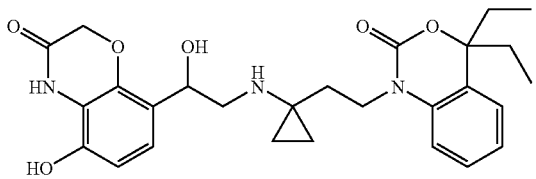

a) 3-(4,4-dimethyl-2-oxo-4H-benzo[d][1,3oxazin-1-yl]-propionitrile 10.2 mL (123 mmol) bromopropionitrile are added dropwise to a solution of 20.0 g (112 mmol) 4,4-dimethyl-1,4-dihydro-benzo[d][1,3]oxazin-2-one and 17.4 g (126 mmol) potassium carbonate in 250 mL acetonitrile and the mixture is refluxed overnight. Another 4 mL (48 mmol) of bromopropionitrile are added and the mixture is refluxed for another 2 hours. The solid is suction filtered, the filtrate is evaporated down and the residue is recrystallised from diisopropylether. White solid.

Yield: 22.8 g (88%); mass spectroscopy: [M+H]$^+$=231.

b) 1-[2-(1-amino-cyclopropyl)-ethyl-4,4-dimethyl-1,4-dihydro-benzo[d][1,3]oxazin-2-one A suspension of 6.0 g (26 mmol) 3-(4,4-dimethyl-2-oxo-4H-benzo[d][1,3]oxazin-1-yl]-propionitrile in 120 mL diethyl ether is combined with 16.5 mL (56 mmol) titanium tetra-isopropoxide while being cooled with an ice bath. Then 18.5 mL of a 3 molar solution of ethylmagnesium bromide in diethyl ether are added dropwise such that the temperature does not climb past 20° C. The mixture is stirred for 30 minutes at ambient temperature and 7.0 mL (55 mmol) boron trifluoride-diethyl ether are added batchwise while cooling with an ice bath. The mixture is stirred for one hour at ambient temperature and 150 mL 1 molar sodium hydroxide solution are added dropwise while cooling. The reaction mixture is diluted with diethyl ether and the phases are separated. The aqueous phase is extracted with diethyl ether and the combined organic phases are extracted with sodium sulphite solution and repeatedly extracted with 1 molar hydrochloric acid. The hydrochloric acid phases are combined, extracted with diethyl ether, made alkaline with sodium hydroxide solution and exhaustively extracted with dichloromethane. The dichloromethane phases are dried with sodium sulphate and evaporated down. Light yellow oil.

Yield: 1.5 g (22%); mass spectroscopy: [M+H]$^+$=261.

c) 1-(2-{1-[2-(5-benzyloxy-3-oxo-3,4-dihydro-2H-benzo[1,4]oxazin-8-yl)-2-hydroxy-ethylamino]-cyclopropyl}-ethyl)-4,4-dimethyl-1,4-dihydro-benzo[d][1,3]oxazin-2-one 900 mg (2.5 mmol) 5-benzyloxy-8-(2-ethoxy-2-hydroxy-acetyl)-4H-benzo[1,4]oxazin-3-one and 700 mg (2.7 mmol) 1-[2-(1-amino-cyclopropyl)-ethyl]-4,4-dimethyl-1,4-dihydro-benzo[d][1,3]oxazin-2-one are dissolved in 20 mL ethanol and stirred in each case for 30 minutes at 80° C. and 50° C. The reaction mixture is cooled, combined with 200 mg (5.3 mmol) sodium borohydride and stirred for 2 hours at ambient temperature. Glacial acetic acid is added, the mixture is stirred for 10 minutes and evaporated down. The residue is taken up in dichloromethane and washed successively with potassium hydrogen sulphate solution, 15% potassium carbonate solution and sodium hydrogen carbonate solution. Then the organic phase is dried with sodium sulphate and freed from solvent. The residue is purified by column chromatography (silica gel; ethyl acetate/methanol/ammonia gradient). Recrystallisation from diisopropylether. White solid.

Yield: 690 mg (49%); mass spectroscopy: [M+H]$^+$=558.

d) 1-(2-{1-[2-hydroxy-2-(5-hydroxy-3-oxo-3,4-dihydro-2H-benzo[1,4]oxazin-8-yl)-ethylamino]-cyclopropyl}-ethyl)-4,4-dimethyl-1,4-dihydro-benzo[d][1,3]oxazin-2-one 650 mg (1.17 mmol) 1-(2-{1-[2-(5-benzyloxy-3-oxo-3,4-dihydro-2H-benzo[1,4]oxazin-8-yl)-2-hydroxy-ethylamino]-cyclopropyl}-ethyl)-4,4-dimethyl-1,4-dihydro-benzo[d][1,3]oxazin-2-one are dissolved in 30 mL methanol, combined with palladium on charcoal (10%) and hydrogenated at ambient temperature and 3 bar hydrogen pressure.

Yield: 240 mg (44%); mass spectroscopy: [M+H]$^+$=468.

EXAMPLE 17

1-(2-{1-[2-hydroxy-2-(6-hydroxy-3-oxo-3,4-dihydro-2H-benzo[1,4]oxazin-8-yl)-ethylamino]-cyclopropyl}-ethyl)-4,4-dimethyl-1,4-dihydro-benzo[d][1,3]oxazin-2-one

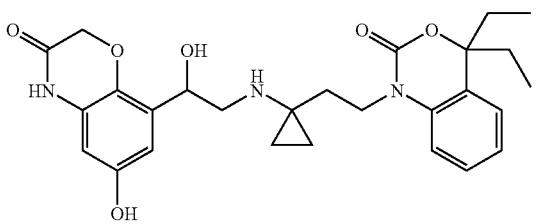

a) 1-(2-{1-[2-(6-benzyloxy-3-oxo-3 4-dihydro-2H-benzo[1,4]oxazin-8-yl)-2-hydroxy-ethylamino]-cyclopropyl}-ethyl)-4,4-dimethyl-1,4-dihydro-benzo[d][1,3]oxazin-2-one Prepared from 900 mg (2.5 mmol) 6-benzyloxy-8-(2-ethoxy-2-hydroxy-acetyl)-4H-benzo[1,4]oxazin-3-one and 700 mg (2.7 mmol) 1-[2-(1-amino-cyclopropyl)-ethyl]-4,4-dimethyl-1,4-dihydro-benzo[d][1,3]oxazin-2-one analogously to the method described for Example 16a. White solid. Yield: 630 mg (45%); mass spectroscopy: [M+H]$^+$=558.

b) 1-(2-{1-[2-hydroxy-2-(6-hydroxy-3-oxo-3,4-dihydro-2H-benzo[1,4]oxazin-8-yl)-ethylamino]-cyclopropyl}-ethyl)-4,4-dimethyl-1,4-dihydro-benzo[d][1,3]oxazin-2-ol 590 mg (1.06 mmol) 1-(2-{1-[2-(6-benzyloxy-3-oxo-3,4-dihydro-2H-benzo[1,4]oxazin-8-yl)-2-hydroxy-ethylamino]-cyclopropyl}-ethyl)-4,4-dimethyl-1,4-dihydro-benzo[d][1,3]oxazin-2-one are dissolved in 30 mL methanol and hydrogenated in the presence of palladium on charcoal (10%) at ambient temperature and 3 bar hydrogen pressure. Yield: 180 mg (36%); mass spectroscopy: [M+H]$^+$=468.

The Examples listed below are obtained analogously to the methods described hereinbefore.

EXAMPLE 18

1-{3-[2-hydroxy-2-(6-hydroxy-3-oxo-3,4-dihydro-2H-benzo[1,4]oxazin-8-yl)-ethylamino]-3-methyl-butyl}-spiro(cyclohexane-1,4'-2H-3',1'-benzoxazin)-2'-one

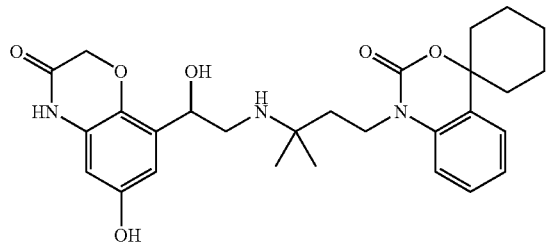

EXAMPLE 19

1-{3-[2-hydroxy-2-(5-hydroxy-3-oxo-3,4-dihydro-2H-benzo[1,4]oxazin-8-yl)-ethylamino]-3-methyl-butyl}-spiro(cyclohexane-1,4'-2H-3',1'-benzoxazin)-2'-one

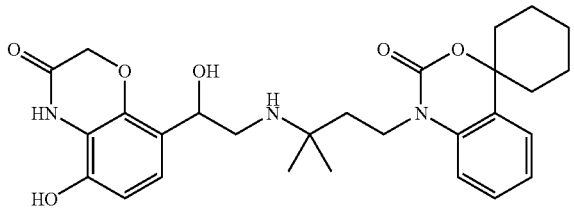

EXAMPLE 20

4,4-dimethyl-1-{3-[2-hydroxy-2-(6-hydroxy-3-oxo-3,4-dihydro-2H-benzo[1,4]oxazin-8-yl)-ethylamino]-propyl}-1,4-dihydro-benzo[d][1,3]oxazin-2-one

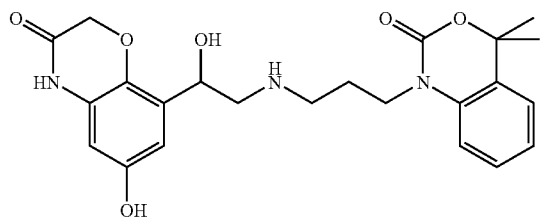

EXAMPLE 21

4,4-dimethyl-1-{3-[2-hydroxy-2-(5-hydroxy-3-oxo-3,4-dihydro-2H-benzo[1,4]oxazin-8-yl)-ethylamino]-propyl}-1,4-dihydro-benzo[d][1,3]oxazin-2-one

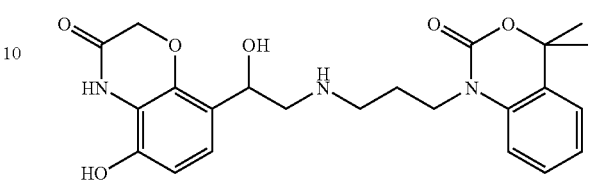

As has been found, the compounds of general formula 1 are characterised by their range of uses in the therapeutic field. Particular mention should be made of those applications for which the compounds of formula 1 according to the invention may preferably be used on the basis of their pharmaceutical activity as betamimetics.

These include, for example, the treatment of inflammatory and obstructive respiratory complaints, preferably the treatment of asthma or COPD (chronic obstructive pulmonary disease), the inhibition of premature labour in midwifery (tocolysis), the restoration of the sinus rhythm in the heart in cases of atrio-ventricular block as well as the correcting of bradycardic heart rhythm disorders (antiarrhythmic agent), the treatment of circulatory shock (vasodilatation and increasing the heart-time volume) as well as the treatment of itching and skin inflammation.

In one aspect the present invention relates to the use of the compounds of formula 1 as pharmaceutical compositions. In another aspect the present invention relates to the use of the compounds of formula 1 for preparing a pharmaceutical composition for the treatment of diseases, wherein therapeutically effective doses of a betamimetic can deliver a therapeutic benefit. It is particularly preferable to use compounds of formula 1 for preparing a pharmaceutical composition for the treatment of inflammatory and obstructive respiratory complaints, particularly preferably the treatment of asthma or COPD, for inhibiting premature labour in midwifery (tocolysis), for restoring the sinus rhythm in the heart in cases of atrio-ventricular block, for correcting bradycardic heart rhythm disorders, for treating circulatory shock (vasodilatation and increasing the heart-time volume) and for the treatment of itching and skin inflammation. It is particularly preferred according to the invention to use compounds of formula 1 for preparing a pharmaceutical composition for the treatment of inflammatory and obstructive respiratory complaints, particularly preferably for the treatment of asthma or COPD. Also of particular importance is the use of compounds of formula 1 as described above for preparing a pharmaceutical composition for a once-a-day treatment of inflammatory and obstructive respiratory complaints, particularly preferably for a once-a-day treatment of asthma or COPD.

Suitable preparations for administering the compounds of formula 1 include for example tablets, capsules, suppositories, solutions, powders, etc. The content of the pharmaceutically active compound(s) should be in the range from 0.05 to 90 wt. -%, preferably 0.1 to 50 wt. -% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

In the preferred use of the compounds of formula 1 for the treatment of asthma or COPD according to the invention it is particularly preferred to use preparations or pharmaceutical formulations which are suitable for inhalation. Inhalable preparations include inhalable powders, propellant-containing metered-dose aerosols or propellant-free inhalable solutions Within the scope of the present invention, the term propellant-free inhalable solutions also includes concentrates or sterile ready-to-use inhalable solutions. The formulations which may be used within the scope of the present invention are described in more detail in the next part of the specification The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 μm, more preferably from 1 to 5 μm, is added to the excipient mixture. Processes for producing the inhalable powders according to the invention by grinding and micronising and lastly mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution.

The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 20 to mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the milligram range, for example.

In another aspect the present invention relates to the above-mentioned pharmaceutical formulations as such, which are characterised in that they contain a compound of formula 1, particularly preferably the above-mentioned pharmaceutical formulations administered by inhalation.

The following examples of formulations illustrate the present invention without restricting its scope:

Examples of Pharmaceutical Formulations

| A) Tablets | per tablet |
| --- | --- |
| active substance of formula 1 | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
| --- | --- |
| active substance of formula 1 | 80 mg |
| lactose | 55 mg |
| maize starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance of formula 1 | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| D) Metered-dose aerosol | |
|---|---|
| active substance of formula 1 | 0.005 |
| sorbitolan trioleate | 0.1 |
| monofluorotrichloromethane and TG134a:TG227 2:1 | ad 100 |

The suspension is transferred into a conventional aerosol container with a metering valve. Preferably, 50 μl of suspension are delivered per spray. The active substance may also be metered in higher doses if desired (e.g. 0.02% by weight).

| F) Powder for inhalation | |
|---|---|
| active substance of formula 1 | 12 μg |
| lactose monohydrate | ad 10 mg |

The powder for inhalation is produced in the usual way by mixing the individual ingredients together.

What is claimed is:

1. A compound of formula 1″

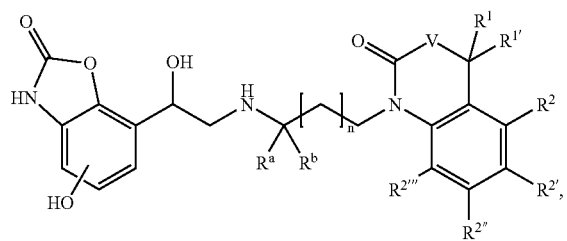

wherein:
V is —$CH_2$—, —NH—, or —O—;
$R^a$ and $R^b$ are each independently hydrogen, $C_{1-4}$-alkyl, or halogen-$C_{1-4}$-alkyl, or
$R^a$ and $R^b$ together are a $C_{2-5}$-alkylene bridge wherein one or more hydrogen atoms are optionally replaced by halogen;
$R^1$ and $R^{1'}$ are each independently hydrogen, $C_{1-6}$-alkyl, $C_{3-6}$-cycloalkyl, halogen-$C_{1-6}$-alkyl, halogen-$C_{3-6}$-cycloalkyl, or $C_{1-6}$-alkylene-$C_{3-6}$-cycloalkyl, or
$R^1$ and $R^{1'}$ together are a $C_{2-5}$-alkylene bridge wherein one or more hydrogen atoms are optionally replaced by halogen;
$R^2$, $R^{2'}$, $R^{2''}$, and $R^{2'''}$ are each independently hydrogen, $C_{1-6}$-alkyl, halogen-$C_{1-6}$-alkylene, OH, HO—$C_{1-6}$-alkylene, —O—$C_{1-6}$-alkyl, $C_{6-10}$-aryl,-$C_{1-4}$-alkylene, $C_{6-10}$-aryl-$C_{1-6}$-alkylene-O, COOH, COO$C_{1-6}$-alkyl, O—$C_{1-6}$-alkylene-COOH, O—$C_{1-6}$-alkylene-COO$C_{1-6}$-alkyl, NHSO$_2$—$C_{1-6}$-alkyl, CN, NH$_2$, NH—$C_{1-6}$-alkyl, N($C_{1-6}$-alkyl)$_2$, NO$_2$, S—$C_{1-6}$-alkyl, SO$_2$—$C_{1-6}$-alkyl, SO—$C_{1-6}$-alkyl, O(CO)$C_{1-6}$-alkyl, COC$_{1-6}$-alkyl, NHCOC$_{1-6}$-alkyl, or halogen; and
n is 0, 1, or 2,
or an optical isomer thereof, or a corresponding acid addition salt thereof with a pharmacologically acceptable acid.

2. The compound of formula 1″ according to claim 1, wherein:
V is —$CH_2$— or —O—;
$R^a$ and $R^b$ are each independently hydrogen, $C_{1-4}$-alkyl, or halogen-$C_{1-4}$-alkyl, or
$R^a$ and $R^b$ together are a $C_{2-5}$-alkylene bridge wherein one or more hydrogen atoms are optionally replaced by halogen;
$R^1$ and $R^{1'}$ are each independently hydrogen, methyl, ethyl, propyl, or cyclopropyl, or
$R^1$ and $R^{1'}$ together are —$CH_2$—$CH_2$—$CH_2$—$CH_2$— or —$CH_2CH_2$—$CH_2$—$CH_2$—$CH_2$—;
$R^2$ and $R^{2'''}$ are each hydrogen; and
$R^{2'}$ and $R^{2''}$ are each independently hydrogen, methyl, CF$_3$, OH, methyloxy, benzyloxy, COOH, COOCH$_3$, or fluorine,
or an optical isomer thereof, or a corresponding acid addition salt thereof with a pharmacologically acceptable acid.

3. A compound of formula 1‴

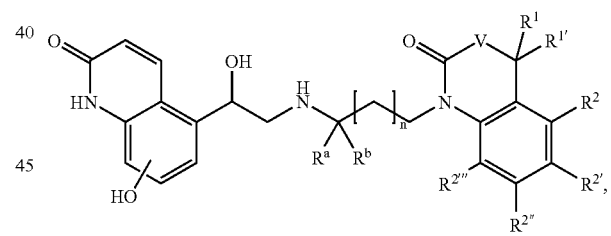

wherein:
V is —$CH_2$—, —NH—, or —O—;
$R^a$ and $R^b$ are each independently hydrogen, $C_{1-4}$-alkyl, or halogen-$C_{1-4}$-alkyl, or
$R^a$ and $R^b$ together are a $C_{2-5}$-alkylene bridge wherein one or more hydrogen atoms are optionally replaced by halogen;
$R^1$ and $R^{1'}$ are each independently hydrogen, $C_{1-6}$-alkyl, $C_{3-6}$-cycloalkyl, halogen-$C_{1-6}$-alkyl, halogen-$C_{3-6}$-cycloalkyl, or $C_{1-6}$-alkylene-$C_{3-6}$-cycloalkyl, or
$R^1$ and $R^{1'}$ together are a $C_{2-5}$-alkylene bridge wherein one or more hydrogen atoms are optionally replaced by halogen;
$R^2$, $R^{2'}$, $R^{2''}$ and $R^{2'''}$ are each independently hydrogen, $C_1$-alkyl, halogen-$C_{1-6}$-alkylene, OH, HO—$C_{1-6}$-alkylene, —O—$C_{1-6}$-alkyl, $C_{6-10}$, -aryl-$C_{1-4}$-alkylene, $C_{6-10}$-aryl-$C_{1-6}$-alkylene-O, COOH, COO$C_{1-6}$-alkyl, O—$C_{1-6}$-alkylene-COOH, O—$C_{1-6}$-alkylene- COOC$_{1-6}$-alkyl, NHSO$_2$—C$_{1-6}$-alkyl, CN, NH$_2$, NH—C$_{1-6}$-alkyl, N(C$_{1-6}$-alkyl)NO$_2$, S—C$_{1-6}$-alkyl, SO$_2$—C$_{1-6}$-alkyl, O(CO)C$_{1-6}$-alkyl, COC$_{1-6}$-alkyl, NHCOC$_{1-6}$-alkyl, or halogen; and n is 0, 1, or 2, or an optical isomer thereof, or a corresponding acid addition salt thereof with a pharmacologically acceptable acid.

4. The compound of formula 1''' according to claim 3, wherein:

V is —CH$_2$— or —O—;

R$^a$ and R$^b$ are each independently hydrogen, -C$_{1-4}$-alkyl, or

R$^a$ and R$^b$ together are a C$_{2-5}$-alkylene-$_{13}$ bridge wherein one or more hydrogen atoms are optionally replaced by halogen;

R$^1$ and R$_{1'}$ are each independently hydrogen, methyl, ethyl, propyl, or cyclopropyl, or R$^1$ and R$^{1'}$ together are —CH$_2$—CH$_2$—, —CH$_2$—CH$_2$—CH$_2$—C$_2$—, or —CH$_2$—CH$^2$—CH$_2$—CH$_2$—CH$_2$—;

R$^2$ and R$^{2'''}$ are each hydrogen; and

R$^{2'}$ and R2" are each independently hydrogen, methyl, CF$_3$, OH, methyloxy, benzyloxy, COOH, COOCH$_3$, or fluorine, an optical isomer thereof, or the corresponding acid addition salt thereof with a pharmacologically acceptable acid.

5. A compound of formula 1'''' wherein:

V is —CH$_2$—, NH—, or —O—;

R$^a$ and R$^b$ are each independently hydrogen, C$_{1-4}$-alkyl, or halogen-C$_{1-4}$-alkyl, or R$^a$ and R$^b$ together are a C$_{2-5}$-alkylene bridge wherein one or more hydrogen atoms are optionally replaced by halogen;

R$_1$ and R$_{1'}$ are each independently hydrogen, C$_{1-6}$-alkyl, C$_{3-6}$-cycloalkyl, halogen-C$_{1-6}$-alkyl, halogen-C$_{3-6}$-cycloalkyl, or C$_{1-6}$-alkylene-C$_{3-6}$-cycloalkyl, or R$^1$ and R$^{1'}$ together are a C$_{2-5}$-alkylene bridge wherein one or more hydrogen atoms are optionally replaced by halogen;

R$^2$, R$^{2'}$, and R$^{2'''}$, are each independently hydrogen, C$_{1-6}$alkyl, halogen-C$_{1-6}$-alkylene, OH, HO—C$_{1-6}$-alkylene, —O—C$_{1-6}$-alkyl, c$_{6-10}$-aryl-C$_{1-4}$-alkylene, C$_{6-10}$-aryl-C$_{1-6}$-alkylene-O, COOH, COOC$_{1-6}$-alkyl, O—C$_{1-6}$-alkylene-COOH, O—C$_{1-6}$-alkylene-COOC$_{1-6}$-alkyl, NHSO$_2$—C$_{1-6}$-alkyl, CN, NH$_2$, NH—C$_{1-6}$-alkyl, N(C$_{1-6}$-alkyl)$_2$, NO$_2$, S—C$_{1-6}$-alkyl, SO$_2$—C$_{1-6}$-alkyl, SO—C$_{1-6}$-alkyl , O(CO)C$_{1-6}$-alkyl, COC$_{1-6}$-alkyl, NHCOC$_{1-6}$-alkyl, or halogen; and is 0, 1, or 2, or an optical isomer thereof, or a corresponding acid addition salt thereof with a pharmacologically acceptable acid thereof.

6. The compound of formula 1'''' according to claim 5, wherein:

V is —CH$_2$—and —O—;

R$^a$ and R$^b$ are each independently hydrogen, C$_{1-4}$-alkyl, and halogen-C$_{1-4}$-alkyl, or R$^a$ and R$^b$ together are a C$_{2-5}$-alkylene-_bridge wherein one or more hydrogen atoms are optionally replaced by halogen;

R$^1$ and R$^{1'}$ are each independently hydrogen, methyl, ethyl, propyl, cyclopropyl, or R$^1$ and R$^{1'}$ together are —CH$_2$—CH$_2$—CH$_2$—CH$_2$— or CH$_2$—CH$_2$—CH$_2$—CH$_2$—CH$_2$—;

R$^2$ and R$^{2'''}$ are each hydrogen; and

R$^{2'}$ and R$^{2''}$ are each independently hydrogen, methyl, CF$_3$, OH, methyloxy, benzyloxy, COOH, COOCH$_3$, or fluorine, an optical isomer thereof, or a corresponding acid addition salt thereof with a pharmacologically acceptable acid.

7. A pharmaceutical composition comprising the compound of formula 1'' according to claim 1 and a pharmaceutically acceptable carrier or excipient thereof.

8. A pharmaceutical composition comprising two or more compounds of formula 1'' according to claim 1 and a pharmaceutically acceptable carrier or excipient thereof.

9. The pharmaceutical composition according to claim 7 or claim 8, wherein the pharmaceutical composition is administered by inhalation.

10. A pharmaceutical composition according to claim 9, which is in the form of an inhalable powder, propellant-containing metered-dose aerosol or propellant-free inhalable solution.

* * * * *